US008300768B2

United States Patent
Hashimoto et al.

(10) Patent No.: US 8,300,768 B2
(45) Date of Patent: Oct. 30, 2012

(54) X-RAY TUBE AND X-RAY CT APPARATUS

(75) Inventors: Susumu Hashimoto, Kawasaki (JP);
Toyomasa Honda, Nasushiobara (JP);
Sanae Harada, Nasushiobara (JP);
Hiroaki Miyazaki, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 266 days.

(21) Appl. No.: 12/868,437

(22) Filed: Aug. 25, 2010

(65) Prior Publication Data
US 2011/0051884 A1  Mar. 3, 2011

(30) Foreign Application Priority Data

Aug. 28, 2009  (JP) ................. 2009-198563

(51) Int. Cl.
*H01J 35/00* (2006.01)
(52) U.S. Cl. .......................... 378/121; 378/4
(58) Field of Classification Search ............. 378/4–20, 378/119, 121, 122, 136, 137; 313/446, 447, 313/452, 456
See application file for complete search history.

(56) References Cited

U.S. PATENT DOCUMENTS

| 2005/0029957 A1 | 2/2005 | Lemaitre et al. ............. 315/160 |
| 2008/0043916 A1 | 2/2008 | Lemaitre ...................... 378/113 |

FOREIGN PATENT DOCUMENTS

| JP | 2005-56843 | 3/2005 |
| JP | 2006-516206 | 6/2006 |
| JP | 2007-165236 | 6/2007 |
| JP | 2008-43762 | 2/2008 |
| JP | 2009-158138 | 7/2009 |
| JP | 2009-11863 | 11/2009 |
| WO | WO 2004/061864 A2 | 7/2004 |

*Primary Examiner* — Courtney Thomas
(74) *Attorney, Agent, or Firm* — Oblon, Spivak, McClelland, Maier & Neustadt, L.L.P.

(57) ABSTRACT

An X-ray tube includes: a Wehnelt electrode having a dent inside; a filament arranged in the dent of the Wehnelt electrode and configured to emit an electron beam when electricity is passed therethrough; an anode configured to emit an X-ray in response to the incident electron beam; an electrode part configured by at least one pair of electrode members, the electrode members facing each other across a path of the electron beam, a voltage being applied to each of the electrode members; a voltage controller configured to control the voltage applied to the electrode part; and a shield member arranged in contact with the Wehnelt electrode and configured to cover part of the dent by a projecting part.

9 Claims, 16 Drawing Sheets

X-RAY TUBE AND X-RAY CT APPARATUS

CROSS-REFERENCE TO RELATED APPLICATION

This application is based upon and claims the benefit of priority from Japanese Patent Application No. 2009-198563, filed on Aug. 28, 2009; the entire content of which is incorporated herein by reference.

FIELD

Embodiments described herein relate generally to an X-ray tube that emits an X-ray by a combination of a filament and an anode.

BACKGROUND

An X-ray CT apparatus is an image diagnosis apparatus that irradiates, mainly, radiates an X-ray to detect transmission thereof through a subject and reconstructs an image of the inside of the subject from projection data indicating the intensity of the radiation having been detected. Such an X-ray CT apparatus has rapidly become popular on the frontiers of medicine and, as an indispensable diagnosis apparatus to medical practice, plays an important role in many medical practices including diagnosis of disease and plan of treatment and operation. Also for industrial X-ray inspection apparatuses, CT is commercialized by a like principle. In principle, by utilizing the X-ray's property of passing through a subject, X-ray CT apparatuses radiate an X-ray to a subject from multiple directions, measure projection data by a detector arranged on the opposite side across the subject, and reconstruct an image as a cross-sectional image.

To be specific, a medical X-ray CT apparatus executes slice projection by rotating an X-ray tube serving as an X-ray generation source and a detector arranged on the opposite side thereto across a subject at high speeds while sliding the patient, and measures X-ray projection data to compose a cross-sectional image. Such a medical X-ray CT apparatus has been required to reduce the amount of an X-ray administered to a patient, increase an imaging speed, and increase resolution. For this purpose, the medical X-ray CT apparatuses are provided with a diagnostic technique that realizes high speed and high resolution by a multi-slice technique, an ultrahigh-speed image processing technique, and so on. Moreover, industrial X-ray CT apparatuses generally employ a method of, with an X-ray generator and a detector arranged on the opposite side thereto across a subject fixed, rotating the subject to measure projection data and composing a cross-sectional image.

An X-ray tube serving as an X-ray generation source of an X-ray CT apparatus has an electronic optical system that generates an electron beam, and is configured to make the electron beam emitted from the electronic optical system collide with an anode that rotates high speeds and to generate an X-ray by anode collision. The X-ray generator in the X-ray CT apparatus is composed of the X-ray tube that generates an X-ray by the aforementioned configuration. In the following description: in a case that a coil filament is used as an electronic optical system, a longitudinal direction of the filament shall be an X-axis direction, a travelling direction of an electron beam emitted from the electronic optical system of the X-ray tube shall be a Z-axis direction, and a direction orthogonal to both the X-axis and the Z-axis shall be a Y-direction.

In recent years, in accordance with improvement of X-ray CT apparatuses, it has been desired to develop a next-generation CT scanner that responds to increase of resolution, reduction of pseudo defects and increase of a diagnosis function, by adding a function of varying and moving a focal point to the X-ray generation source (the X-ray tube) used with a fixed focal point. A real focal point of an X-ray CT apparatus refers to a place at which electrons collide with an anode and an X-ray is generated, and coincides with a radiation range of an electron beam on the anode.

An X-ray tube of an X-ray CT apparatus is generally used with a fixed focal point. By slightly moving an electron beam (an X-ray beam) reaching an anode in the orthogonal directions to the body axis of a subject laid on a detection system (the X-axis/Y-axis directions), it is possible to increase spatial resolution of projection data obtained by detecting the radiated X-ray.

DETAILED DESCRIPTION

Embodiments described herein aims to provide an X-ray tube that is capable of controlling change of a radiation range of an electron beam on an anode and movement of the path of the electron beam, that prevents radiation of the electron beam radiated to the anode from blurring and that realizes a compact-size X-ray source, and also provide an X-ray CT apparatus using the X-ray tube.

According to this embodiment, an X-ray tube includes: a Wehnelt electrode having a dent inside; a filament arranged in the dent of the Wehnelt electrode and configured to emit an electron beam when electricity is passed therethrough; an anode configured to emit an X-ray in response to the incident electron beam; an electrode part configured by at least one pair of electrode members, the electrode members facing each other across a path of the electron beam, and a voltage being applied to each of the electrode members; a voltage controller configured to control the voltage applied to the electrode part; and a shield member arranged in contact with the Wehnelt electrode and configured to cover part of the dent by a projecting part.

First Embodiment

Below, an X-ray tube according to a first embodiment of the present invention and an X-ray CT apparatus using the X-ray tube will be described. Hereinafter, the configuration of the X-ray tube will be firstly described, and then the entire X-ray CT apparatus will be described. In the following description: a longitudinal direction of a coil filament described later, that is, a vertical direction on paper of FIG. 1 shall be an X-axis direction; a travelling direction of an electron beam emitted from an electronic system of the X-ray tube, that is, a horizontal direction on paper of FIG. 1 shall be a Z-direction; and an orthogonal direction to both the X-axis and the Z-axis, that is, a normal direction of paper of FIG. 1 shall be a Y-axis direction.

Further, the following description will refer to change of the size of a radiation range on the anode to which electrons are radiated and movement of the path of an electron beam radiated to the anode (also referred to as movement of an electron beam). As mentioned before, a real focal point in an X-ray CT apparatus generally refers to a place at which electrons collide with an anode and an X-ray is generated. In other words, it is possible to change the size of the real focal point by changing the size of the radiation range, and it is possible to move the real focal point by moving the path of the electron beam.

(X-Ray Tube)

Figure 1:
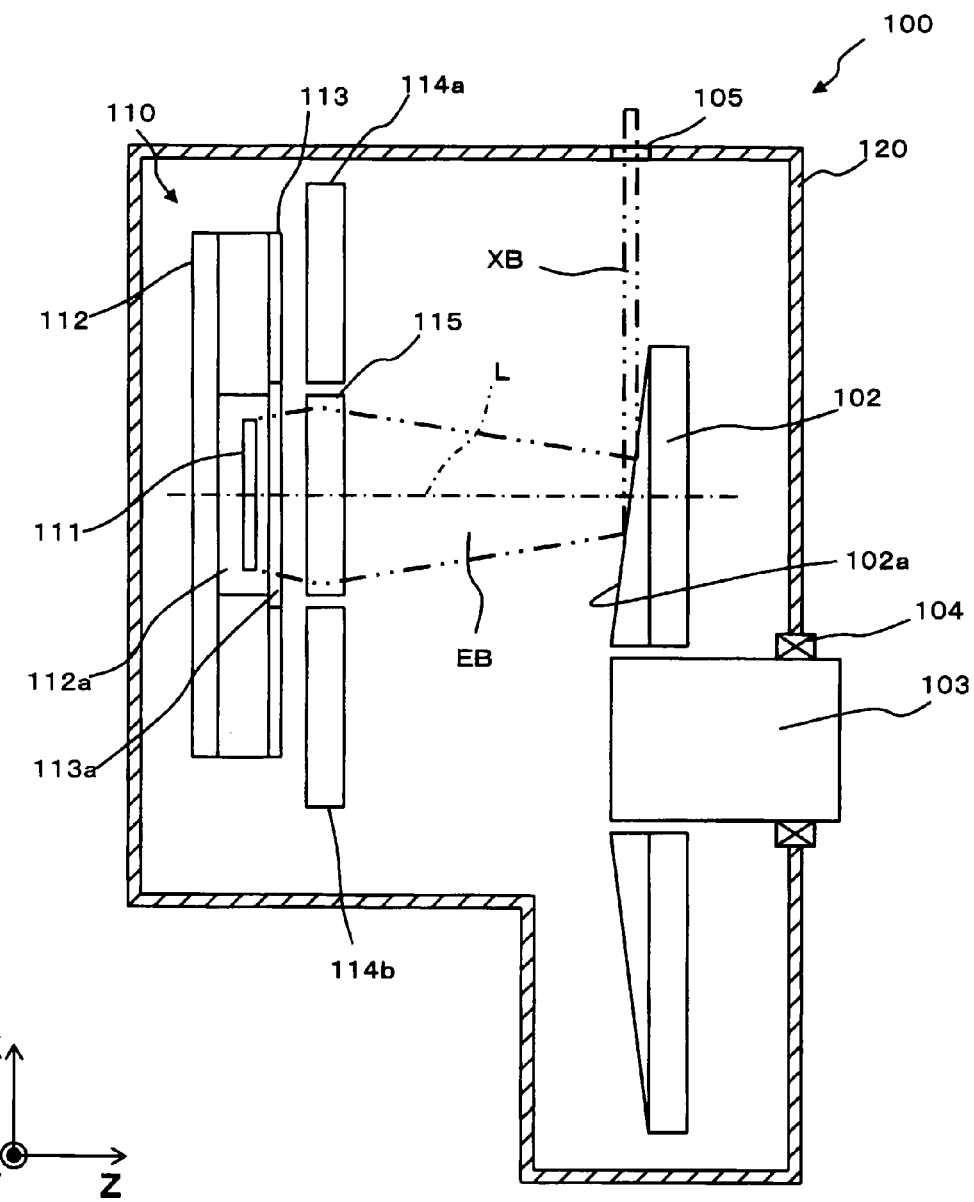
FIG. 1 is a cross-sectional view on the XZ plane of an X-ray tube in the state of radiating an X-ray according to a first embodiment.
Figure 2:
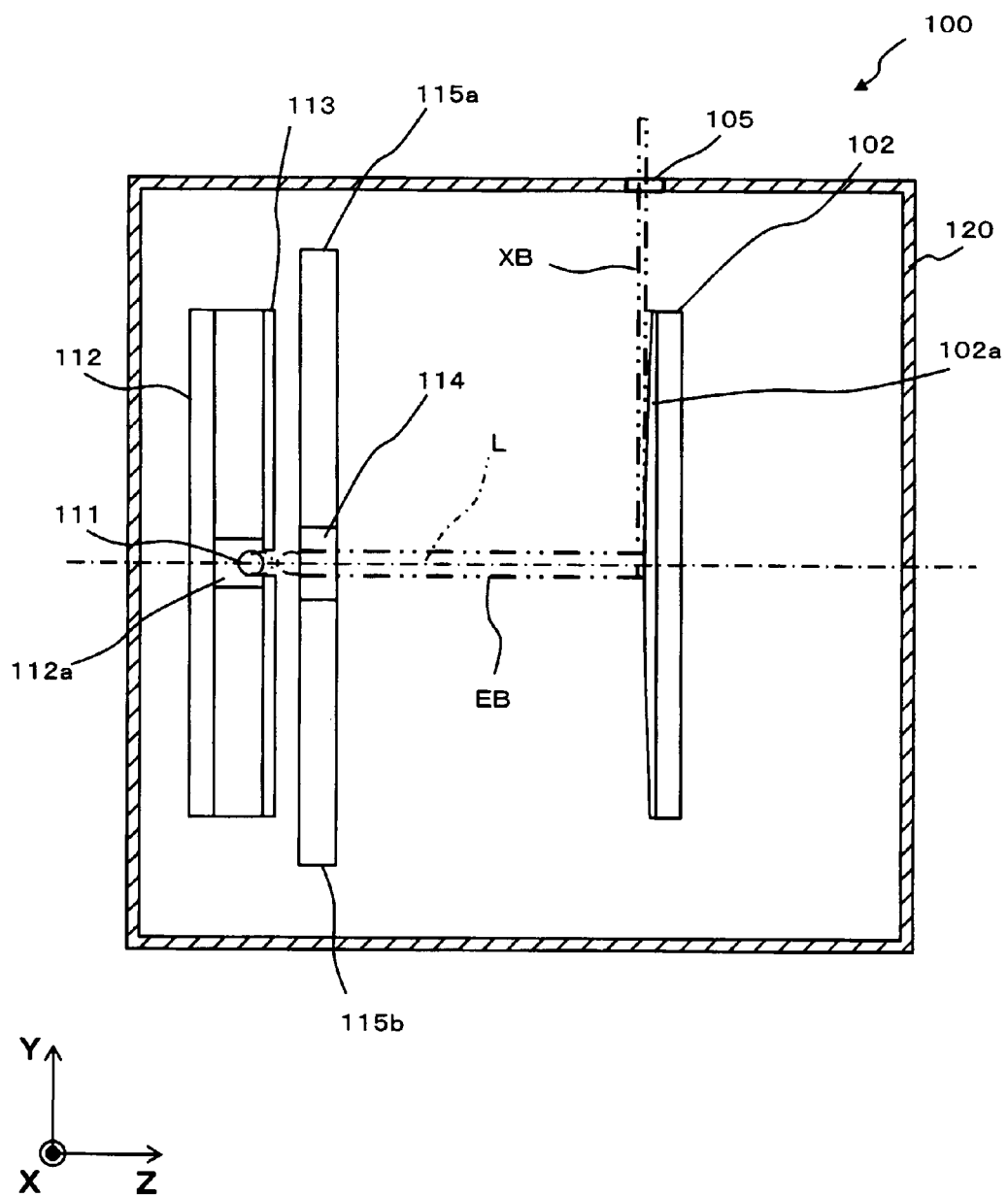
FIG. 2 is a cross-sectional view on the YZ plane of the X-ray tube in the state of radiating an X-ray according to the first embodiment.

FIG. 1 is a cross-sectional view on the XZ plane of the X-ray tube according to this embodiment in the state of radiating an X-ray. Further, FIG. 2 is a cross-sectional view on the YZ plane of the X-ray tube according to this embodiment in the state of radiating an X-ray.

An X-ray tube 100 receives supply of a filament heating current and application of a high voltage and generates an X-ray. As shown in FIG. 1, this X-ray tube 100 is provided with: an electron gun (a coil filament electron gun) 110 that has a coil filament 111 emitting thermo electrons when electricity is passed therethrough; and an anode 102 that radiates an X-ray when irradiated with the electrons emitted by the coil filament 111. The electron gun 110 and the anode 102 are sealed within a shield 120.

The electron gun 110 includes the coil filament 111, a Wehnelt electrode 112, an aperture 113, a pair of X-electrodes 114a and 114b (generically referred to as X-electrodes 114, and also referred to as first electrode members hereinafter), and a pair of Y-electrodes 115a and 115b (generically referred to as Y-electrodes 115, and also referred to as second electrode members hereinafter). The X-electrodes 114 and the Y-electrodes 115 may be referred to as "XY-electrodes" together.

In the electron gun 110, the coil filament 111 is placed on the perpendicular extended down along the −Z-axis direction from the opening formed by the X-electrodes 114 and the Y-electrodes 115 described later. Upon reception of supply of a filament heating current and application of a high voltage to the coil filament 111, the electron gun 110 emits electrons from the opening onto a path L in the +Z-axis direction. The path L is a straight line shown by a dash-dot line in FIG. 1.

The anode 102 is formed in one body with a rotation member 103 extending in the Z-axis direction, and arranged on the path L connecting the coil filament 111 and the opening. To the surface of the anode 102 on the path L, an electron beam emitted from the electron gun 110 is radiated. Then, upon reception of radiation of the electron beam to the surface, the anode 102 emits an X-ray in a direction orthogonal to the path L (a direction orthogonal to the rotation member 103).

Therefore, the shape of the anode 102 is a truncated cone with an upper face facing in the −Z-axis direction, and the normal of a side face 102a corresponding to the surface of the cone is tilted about a few degrees with respect to the path L, for example. Moreover, the rotation member 103 is extended outside the shield 120, and rotated by a motor (not shown in the drawing). A sealing unit 104 is placed between the shield 120 and the rotation member 103. The central axis of the rotation member 103 is shifted in the X-axis direction from the electron beam path L connecting the coil filament 111 and the opening of the electron gun 110. Therefore, the electron beam is radiated to the side face 102a, which is a tilted face of the anode 102. At least part of the side face 22a of the anode 102, to which the electron beam is radiated, is made of tungsten, for example. The shifted direction coincides with the longitudinal direction of the coil filament 111 described later.

In a position of the shield 120 through which the X-ray emitted from the anode 22 passes, a window 105 made of a beryllium film is formed. The X-ray is radiated outside the X-ray tube 100 through this window 105.

In the electron gun 110 of the X-ray tube 100, as shown in FIGS. 1 and 2, the Wehnelt electrode 112, the coil filament 111, the aperture 113 and the XY-electrodes are arranged in this order along an electron beam emission direction (Z-axis direction).

Figure 3:
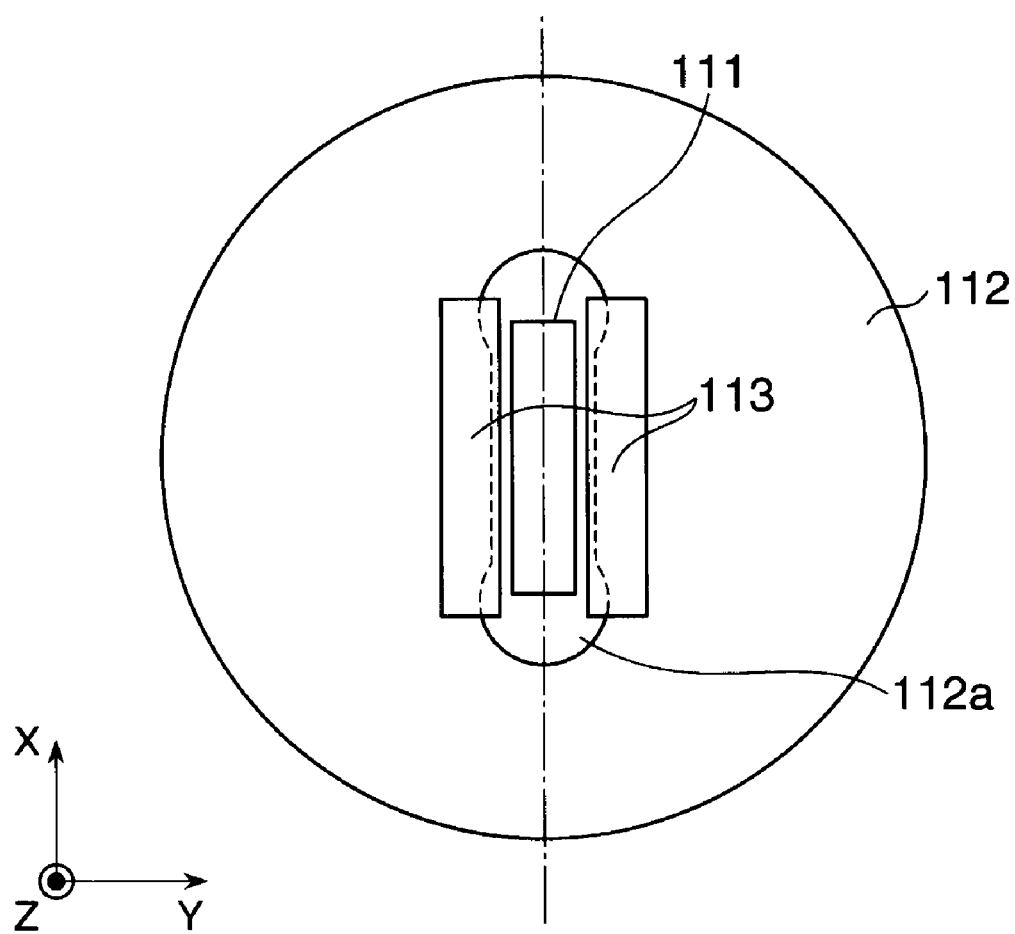
FIG. 3 is a plan view of a Wehnelt electrode seen from the anode side.

FIG. 3 is a plan view of the Wehnelt electrode seen from the anode side. As shown in FIG. 3, the Wehnelt electrode 112 is a disk-like member made of a nonmagnetic metal such as stainless steel, which forms the electrode. The Wehnelt electrode 112 has a groove 112a on a face on the side of the anode 102. In this embodiment, the groove 112a has a rectangular shape with both ends bulge out as shown in FIG. 3. The central axis in the longitudinal direction (X-axis direction) of the groove 112a coincides with the central axis in the longitudinal direction of the coil filament 111. Besides, the center of the Wehnelt electrode 112 coincides with the path L.

Although there are various shapes of Wehnelt electrodes 112, a shape surrounding the filament is common. As described later, a voltage applied to the Wehnelt electrode 112 is lower than a voltage applied to the anode 102, and an electric field is thus formed between the Wehnelt electrode 112 and the anode 102. The Wehnelt electrode 112 causes a radiation range of the electron beam radiated from the coil filament 111 to converge by the electric field generated by the shape thereof surrounding the coil filament 111. That is to say, an inward electric field is given to the electron beam radiated from the coil filament 111, and the radiation range of the electron beam is caused to converge by the inward electric field.

Various shapes surrounding the coil filament 111 can be assumed.

One example is a dent formed in the Wehnelt electrode 112, into which the coil filament 111 is placed. This dent may be a hemisphere shape, a square shape, or a thread-like groove. The bottom of the dent is assumed to be closed, but may be a hole or entirely open. In this embodiment, this dent is described as the groove 112a as mentioned above. Additionally, the coil filament 111 is employed as one example of the filament in this description, but it is possible to use various shapes of filaments within such a size range that the filament can be placed in this dent. For example, it is possible to use various shapes such as a circle, a square and a sphere so as to match the shape of the dent.

Thus, the Wehnelt electrode 112 is used to cause an electron beam to converge. The intensity of the electron beam caused to converge by the Wehnelt electrode 112 is not uniform. While the intensity around the center of the electron beam is sufficient, the intensity of the outer part thereof is weak. This part with weak intensity is also radiated as part of the electron beam, and forms part of a focal point width.

However, in the electron beam, a part with strong intensity and a part with weak intensity are mixed. In order to make the radiation intensity of the electron beam uniform, there is a need to exclude the part with weak intensity, and the aperture 113 is used in this embodiment for this purpose. This aperture 113 is arranged on the side in the travelling direction of the electric beam from the Wehnelt electrode 112 and the coil filament 111 as shown in FIG. 3.

The aperture 113 is placed on the side of the anode 102 on the groove 112a from the Wehnelt electrode 112, and has a projecting part that projects out the opening of the groove 112a. This projecting part blocks part of the electron beam. That is to say, the aperture 113 can be called a blocking member that blocks part of the electron beam by the projecting part. The aperture 113 is a plate-like (disk-like in this embodiment) member having an opening 113a. This aperture 113 is a member that limits the range of the emitted electron beam. The opening 113a has a larger width than the groove 112a in the X-axis direction as shown in FIG. 1, while the aperture 113a has a smaller width than the groove 112a in the Y-axis direction as shown in FIG. 2. In this embodiment, the opening 113a has a rectangular shape with both ends in the longitudinal direction bulge out like the groove 112a shown in FIG. 3.

The central axis in the longitudinal direction (X-axis direction) of the opening 113a coincides with the central axis in the longitudinal direction of the groove 112a.

When the shape of the aperture 113 is seen on the XY plane, the arrangement thereof is as shown in FIG. 3. That is to say, the coil filament 111 and the groove 112a are arranged along the X-axis, and the aperture 113 is also arranged on each side of the groove 112a along the length direction. A part held by the apertures 113 on both the sides is the opening 113a. The length in the X-axis direction of the aperture 113 is longer than that of the coil filament 111. In other words, since the ends of the aperture 113 extend more than the ends of the coil filament 111, a blocking effect can be sufficiently exerted at any part along the X-axis of the coil filament 111.

Although such an arrangement that the aperture 113 is in close contact with the Wehnelt electrode 112 is shown in the drawings, the arrangement is not limited thereto. It is possible to consider insertion of another member into between the aperture 113 and the Wehnelt electrode 112. Also in this case, it is possible to consider the aperture 113 to include the inserted other member. Meanwhile, the opening 113a of the aperture 113 may get away from a radiation position of the filament. In such a case, the narrow opening of the groove 112a decreases the radiation range of the electron beam, and the projecting part of the aperture 113 further reduces the radiation range of the electron beam. Consequently, there is a fear that the electron beam is blocked more than enough to simply block the weak part of the electron beam and the radiation intensity is also lowered. In order to avoid such a situation, the projecting part should be arranged in consideration of a relative relation with the position of the coil filament 111. For this, by arranging the projecting part based on the positional relation with the center of the coil filament 111, it is possible to solve the above problem.

As a specific example of the arrangement, in a case that the coil filament 111 has a long shape, the arrangement may be determined based on an angle formed by a line connecting the central axis of the coil filament 111 and the end of the projecting part and a line that passes through the central axis toward the radiation axis direction of the coil filament 111. For example, this angle may be 45 degrees.

The coil filament 111 extends in the same direction as the groove 112a while being wound like a spiral. That is to say, the coil filament 111 is a filament whose longitudinal direction is an extending direction of the groove 112 (X-axis direction). For example, the coil filament 111 is made of tungsten, and emits thermo electrons when electricity is passed therethrough.

The coil filament 111 is placed in the position of the dent (for example, the groove 112a) of the Wehnelt electrode 112. To be specific, the coil filament 111 completely enters the dent. Alternatively, the coil filament 111 may be configured to be half housed in the groove 112a and be partly out the dent. Moreover, the coil filament 111 is not in contact with the Wehnelt electrode.

The coil filament 111 completely fits inside a region formed by the groove 112a and the opening 113a regardless of whether completely enters or partly enters the inside of the groove 112a. In a case that the coil filament 111 protrudes from the region formed by the groove 112a and the opening 113a, the outer part of the electron beam radiated from the coil filament 111 protrudes from a range blocked by the aperture 113.

Such a configuration that the coil filament 111 completely fits the range increases the blocking effect of the projecting part of the aperture 113.

Since the coil filament 111 enters the groove 112a, the size of the opening of the groove 112a is larger than the width of the entering part of the coil filament 111. On the other hand, the size of the opening of the groove 112a is restricted to some range. To be specific, it is desirable that the width of the groove 112a is three times or less the width of the coil filament 111 when seen from a direction in which a pair of electrode members (Y-electrodes 115a and 115b) are formed (namely, from the Y-axis direction). The width of the groove 112a shall be about 1.5 times to 3 times the width of the coil filament 111.

Considering by the area, the size of the opening face of the groove 112a is nine times that of the coil filament 111, and shall be 2.3 times to 9 times.

If the opening of the groove 112a is larger than the above size, an inner wall part that surrounds the coil filament 111 is largely separated from the coil filament 111. Consequently, a force of causing the electron beam radiated from the coil filament 111 to converge by the Wehnelt electrode 112 is weakened. On the contrary, by keeping the size of the groove 112a (the size of the opening of the groove 112a) within the aforementioned range, it is possible to narrow the radiation range of the electron beam to a sufficient range, and it is possible to control the focal point range to a desired size. On the other hand, since the opening does not expand excessively, it is possible to sufficiently increase the effect to block the electron beam to be blocked by the projecting part described later.

Figure 4:
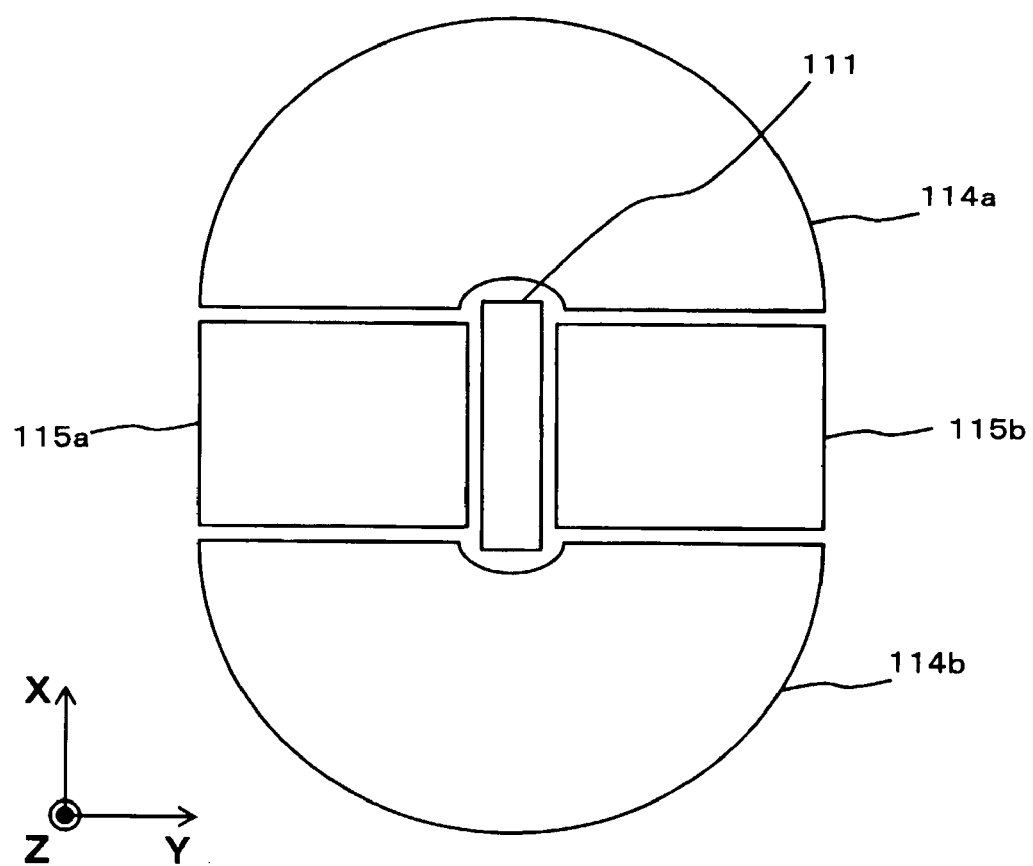
FIG. 4 is a plan view of X-electrodes and Y-electrodes seen from the anode side toward the filament side.

FIG. 4 is a plan view of the X-electrodes and the Y-electrodes seen from the anode side to the filament side. As shown in FIG. 4, the pair of X-electrodes 114a and 114b are placed so as to face each other across the path L, and arranged along the X-axis direction. The distance between the X-electrodes 114a and 114b is longer than the longitudinal length of the coil filament 111. Moreover, the Y-electrodes 115a and 115b are placed so as to face each other across the path L, and arranged along the Y-axis direction. The X-electrodes 114 and the Y-electrodes 115 are arranged on the same plane (the XY plane) (refer to FIG. 4).

To each of the X-electrodes 114, the same electric potential is applied as described later. In a case that the applied voltage is changed, a radiation range $F_{EB}$ of an electron beam on the anode 102 is changed.

In a case that a voltage of one electrode is increased and a voltage of the other electrode is decreased by the same voltage, the path of the electron beam is moved. Also, to each of the Y-electrodes 115, the same electric potential is applied in a like manner. In a case that the applied voltage is changed, the radiation range $F_{EB}$ of the electron beam on the anode 102 is changed. When a voltage of one electrode is increased and a voltage of the other electrode is decreased by an increase, the path of the electron beam moves.

When a voltage is applied, the X-electrodes 114 generate an electric field between the X-electrodes 114a and 114b. The X-electrodes 114 are made of nonmagnetic metal such as stainless steel. The X-electrodes 114 have the same shapes. The shape of each of the X-electrodes 114 is part of a disc around one point on the path L, and the chord extends in the Y-axis direction.

When a voltage is applied, the Y-electrodes 115 generate an electric field between the pair of Y-electrodes 115a and 115b. The Y-electrodes 115 are made of nonmagnetic metal such as stainless steel.

The Y-electrodes 115 have the same shape, which is a rectangular shape.

The Y-electrodes 115 are arranged so as to be held between the X-electrodes 114a and 114b facing each other. To be specific, the X-electrodes 114 and the Y-electrodes 115 are arranged as shown in FIG. 4. There are gaps between the X-electrodes 114 and between the Y-electrodes 115, respectively. A gap through which the electron beam passes is formed by the facing X-electrodes 114 and the facing Y-electrodes 115. In FIG. 4, the coil filament 111 can be seen through the gap formed by the XY-electrodes.

To the Wehnelt electrode 112, the X-electrodes 114a and 114b, and the Y-electrodes 115a and 115b, electric potentials are applied from outside the X-ray tube 100. Moreover, to the coil filament 111, electric power is supplied from outside the X-ray tube 100. The X-electrodes 114a and 114b and the Y-electrodes 115a and 115b are insulated from each other, and the electric potentials thereof can be controlled independently from each other. That is to say, it is possible to apply different electric potential to the respective X-electrodes 114a and 114b, and it is possible to apply different voltages to the respective Y-electrodes 115a and 115b.

Next, the operation of the X-ray tube 100 configured as described above will be described. Firstly, a vacuum is created inside the shield 120. Next, a voltage is applied to between the anode 102 and the Wehnelt electrode 112. At this moment, a voltage applied to the Wehnelt electrode 112 is lower than a voltage applied to the anode 102.

For example, a ground potential is applied to the anode 102, and an electric potential of −tens of kilovolts is applied to the Wehnelt electrode 112. Moreover, a ground potential is applied to the shield 120.

Consequently, an electric field that heads from the Wehnelt electrode 112 to the anode 102 is generated inside the shield 120. The application of the voltage to the Wehnelt electrode 112 is performed by a high-voltage generating device 013 described later. Moreover, control of the value of the voltage applied to the Wehnelt electrode 112 is performed by a scan controller 031.

Further, the electric potential of the coil filament 111 shall be slightly more positive than the electric potential of the Wehnelt electrode 112. In this state, electric power is supplied to the coil filament 111 from outside the X-ray tube 100, and electricity is passed therethrough. Thus, the coil filament 111 is heated to emit thermo electrons.

Figure 5:
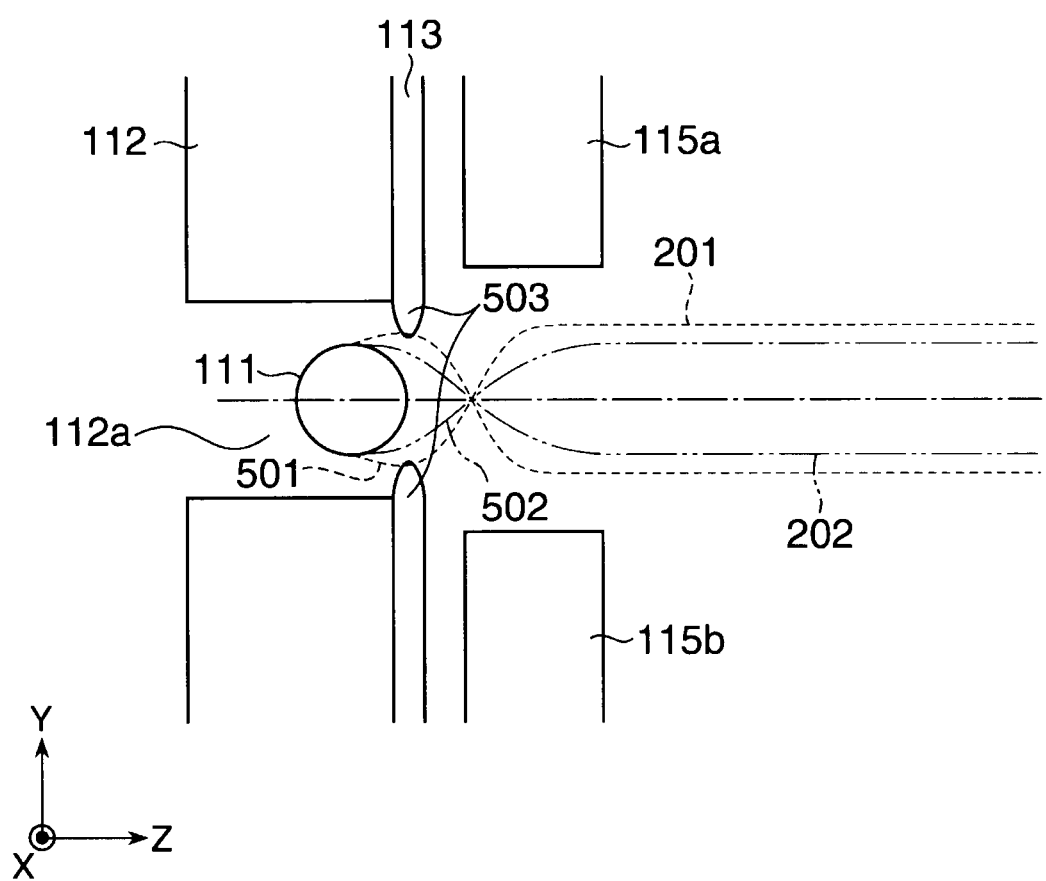
FIG. 5 is a magnified cross-sectional view on the YZ plane of the filament and the neighborhood thereof in the state of radiating an X-ray for describing blockage of an electron beam by an aperture.

As shown in FIG. 5, electrons are emitted from the coil filament 111 as between a dotted line 201 and a dash-dot-dot line 202. As described before, the coil filament 111 is within the region formed by the groove 112a of the Wehnelt electrode 112 and the opening of the aperture 113. A radiation path of the electron beam indicated by the dotted line 201 and the dash-to-dot line 202 is formed by the lens effect by the Wehnelt electrode 112 on the electrons radiated from the coil filament 111. Since the thus formed electron beam is partially blocked by the projecting part 503 of the aperture 113, a part of the electron beam between a dotted line 501 and a dash-dot-dot line 502 will not be radiated to the anode 102 actually. The electron beam of the other region held by the dotted line 501 and the dash-dot-dot line 502 is actually radiated.

As a part becomes closer to the dotted line 501 among the electron beam width, the part becomes closer to the radiated end of the coil filament 111. Thus, the intensity of the electron beam on the side closer to the dotted line 501 is weaker than the intensity of the electron beam on the side closer to the dash-dot-dot line 502. Therefore, the intensity of the electron beam between the dotted line 501 and the dash-dot-dot line 502 is not uniform. By blocking the outer part, namely, a part closer to the dotted line 501 of the electron beam by the projecting part 503 of the aperture 113, the electron beam with weak intensity is blocked. Consequently, it is possible to make the intensity of the electron beam to be obtained uniform. The emitted electrons contract due to the lens effect by the Wehnelt electrode 112, and an electron beam EB is formed along a path L and radiated to a side face 102a of the anode 102.

Another aspect of blockage of the electron beam will be described as follows. The trajectories of electrons in the electron beam are different between at the center (a region held by the two dash-dot-dot lines 502) of a path along the cross section of the coil filament 111 and at the periphery (a region between the dotted line 501 and the dash-dot-dot line 502) of a path along the cross section of the coil filament 111. Therefore, as shown by the dotted line 501, electrons in the region between the dotted line 501 and the dash-dot-dot line 502 form a cross-over at a different position from electrons in the region held by the two dash-dot-dot lines 502, and blur occurs at the focal point on the anode 102. In particular, occurrence of blur outstandingly appears in a case that movement of the path of an electron beam described later is performed.

Accordingly, by using the aperture 113 to at least partially block the electrons in the region between the dotted line 501 and the dash-dot-dot line 502, which result in occurrence of blur, it becomes possible to form a more accurate focal point with less blur. The electron beam in the region held by the two dash-dot-dot line 502 emitted from the coil filament 111, when seen on the YZ plane, crosses over from the Wehnelt electrode 112 to between the XY-electrodes, and the electron beam becomes a substantially parallel beam due to the lens effect of the XY-electrodes described later and heads to the anode 102.

Since an electron beam generated from the coil filament 111 is restricted by the aperture 113 as described above, a tube electric current may be less than in a state that the aperture 113 is not disposed. Thus, a shortfall of the tube electric current restricted by the aperture 113 may be compensated by making the diameter and length of the coil filament 111 larger than in a case that the aperture 113 is not placed.

Figure 6A:
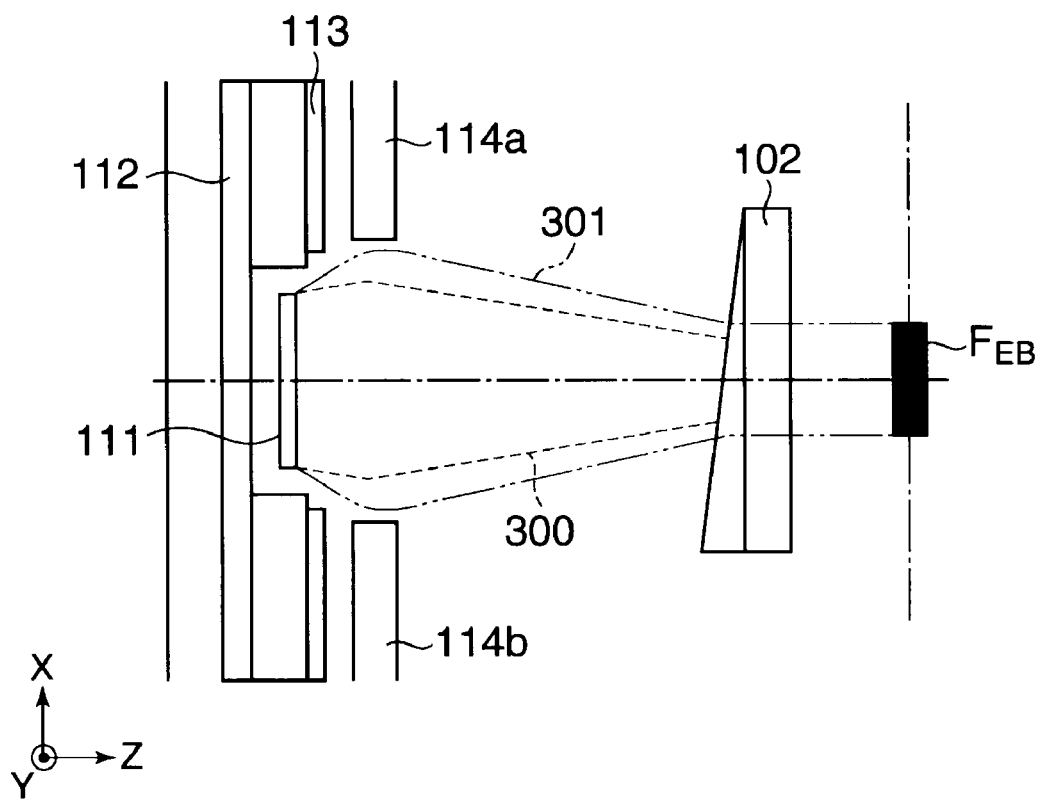
FIG. 6A is a cross-sectional view on the XZ plane in the state of a large-size radiation range.
Figure 6B:
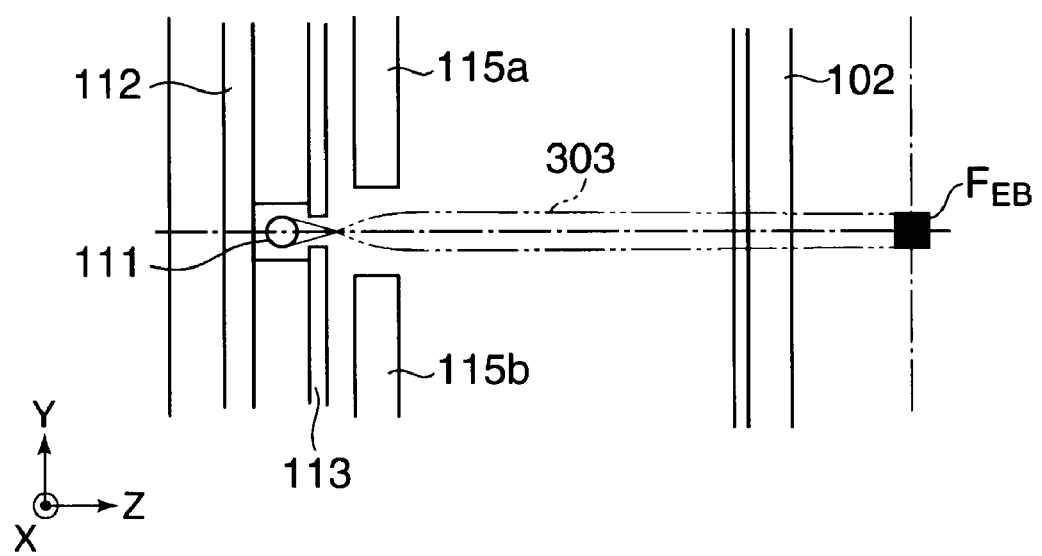
FIG. 6B is a cross-sectional view on the YZ plane in the state of the large-size radiation range.

With reference to FIGS. 6A and 6B, a radiation range $F_{EB}$ will be described. A region on the side face 102a of the anode 102, in which the electron beam EB is radiated, shall be the radiation range $F_{EB}$ (This is also referred to as a real focal point $F_{EB}$ in general. All will be referred to as the radiation range $F_{EB}$ hereinafter.). The shape of the radiation range $F_{EB}$ is a reduced shape of the shape of the coil filament 111.

Consequently, a part of the anode 102 corresponding to the radiation range $F_{EB}$ emits an X-ray. The X-ray reaches a window 105, passes through the window 105, and exits outside the X-ray tube 100.

Thus, the X-ray tube 100 is used as an X-ray source of an X-ray CT apparatus.

This X-ray tube 100 applies electric potentials to the X-electrodes 114a and 114b and the Y-electrodes 115a and 115b, respectively, to form a static electric field. Thus, it is possible to control the size of the radiation range $F_{EB}$, and control the trajectory of the electron beam EB. To be specific, with the electric potential of the Wehnelt electrode 112 as a reference potential, a voltage that an electric potential of several kilovolts or less is added to the reference potential is applied to each of the X-electrodes 114 and Y-electrodes 115. The application of the voltage to the X-electrodes 114a and 114b and the Y-electrodes 115a and 115b is performed by the high-voltage generating device 013 described later. Moreover, control of the voltage applied to the X-electrodes 114a and 114b and the Y-electrodes 115a and 115b is performed by the controller 031.

Figure 7A:
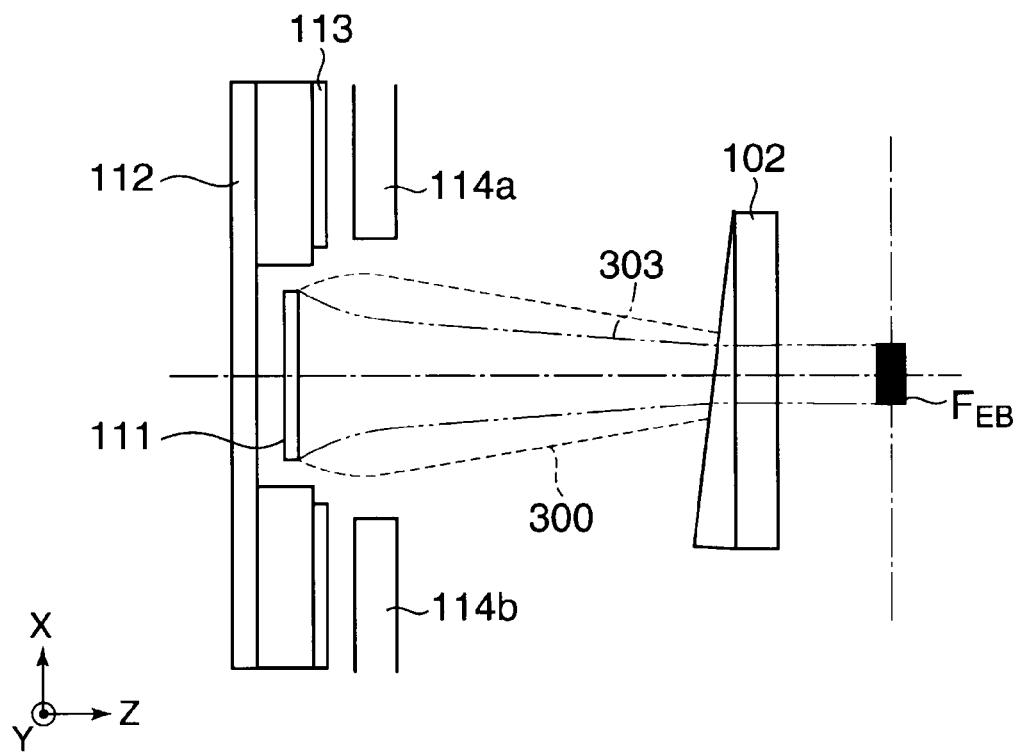
FIG. 7A is a cross-sectional view on the XZ plane in the state of a small-size radiation range.
Figure 7B:
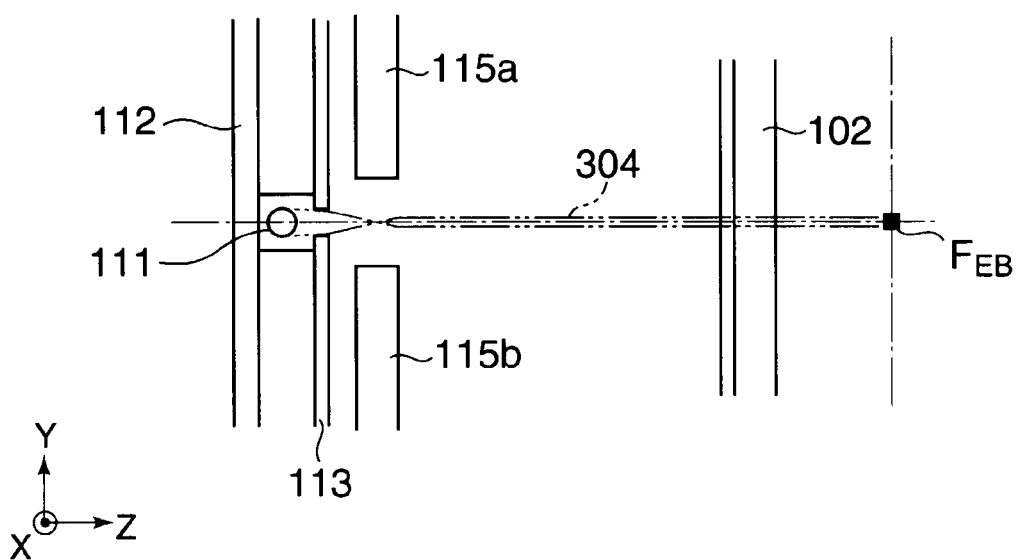
FIG. 7B is a cross-sectional view on the YZ plane in the state of the small-size radiation range.

Firstly, change of the size of the radiation range $F_{EB}$ will be specifically described. FIG. 6A is a cross-sectional view on the XZ plane of the large-size radiation range $F_{EB}$. FIG. 6B is a cross-sectional view on the YZ plane of the large-size radiation range $F_{EB}$. FIG. 7A is a cross-sectional view on the XZ plane of the small-size radiation range $F_{EB}$. FIG. 7B is a cross-sectional view on the YZ plane of the small-size radiation range $F_{EB}$.

A case in which the electric potentials of the X-electrodes 114a and 114b are equal to the electric potential of the Wehnelt electrode 14 shall be a reference (a path indicated by a dotted line in FIG. 6A). For example, to both the X-electrodes 114a and 114b, a voltage to which the same electric potential is added is applied so that both the electric potentials of the X-electrodes 114a and 114b become +2 kilovolts with respect to the electric potential of the Wehnelt electrode 112. Then, as shown in FIG. 6A, it is possible to increase the beam diameter of the electron beam EB in the X-axis direction, and it is possible to increase the size of the radiation range $F_{EB}$ in the X-axis direction.

Also regarding the Y-axis direction, a case in which the electric potentials of the Y-electrodes 115a and 115b are equal to the electric potential of the Wehnelt electrode 112 shall be a reference (not shown).

For example, to both the Y-electrodes 115a and 115b, a voltage to which the same electric potential is added is applied so that both the electric potentials of the Y-electrodes 115a and 115b become +2 kilovolts with respect to the electric potential of the Wehnelt electrode 112. Then, as shown in FIG. 6B, it is possible to increase the beam diameter of the electron beam EB in the Y-axis direction, and it is possible to increase the size of the radiation range $F_{EB}$ in the Y-axis direction.

On the contrary, to both the X electrodes 114a and 114b, a voltage that the same electric potential is subtracted from the electric potential of the Wehnelt electrode 112 is applied. Then, as shown in FIG. 7A, it is possible to decrease the beam diameter of the electron beam EB in the X-axis direction, and it is possible to decrease the size of the radiation range $F_{EB}$ in the X-axis direction.

Also regarding the Y-axis direction, to both the Y-electrodes 115a and 115b, a voltage that the same electric potential is subtracted from the electric potential of the Wehnelt electrode 112 is applied. Then, as shown in FIG. 7B, it is possible to decrease the beam diameter of the electron beam EB in the Y-axis direction, and it is possible to decrease the size of the radiation range $F_{EB}$ in the Y-axis direction.

Figure 8:
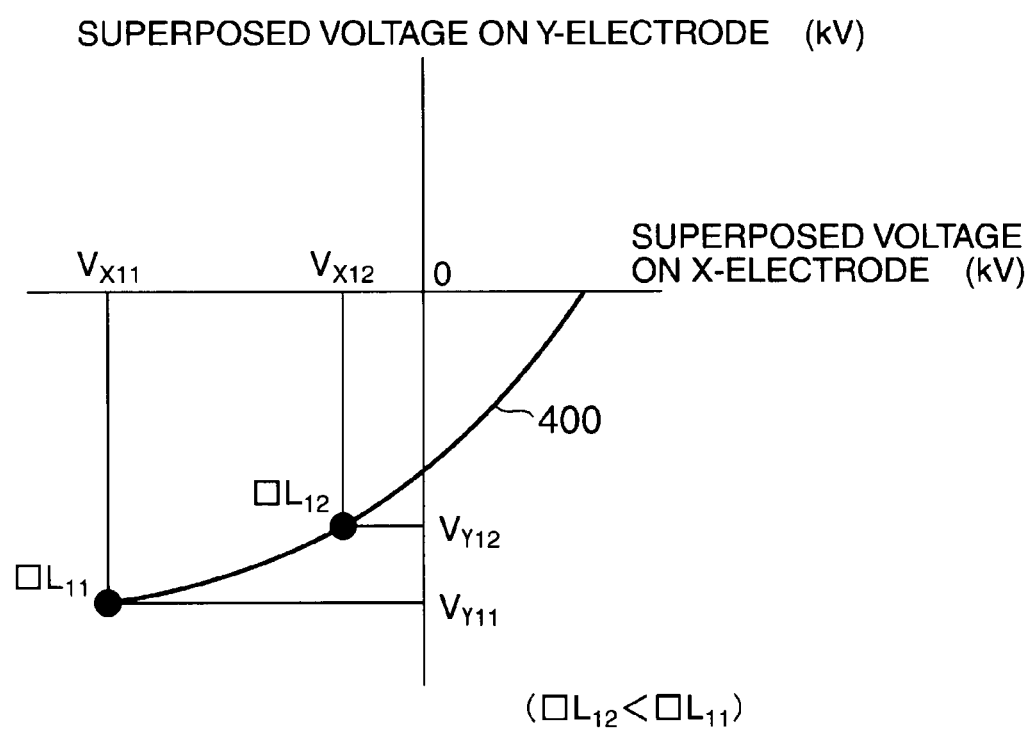
FIG. 8 is a graph showing a relation between voltages superposed on the voltages of the XY-electrodes with respect to a reference voltage and the size of a radiation range at this moment.

A relation between voltages applied to the XY-electrodes and the size of the radiation range $F_{EB}$ will be described. FIG. 8 is a graph showing a relation between voltages superposed on the voltages of the XY-electrodes with respect to a reference voltage and the size of a radiation range at this moment. FIG. 8 is a graph in which the vertical axis takes voltages (kV) applied to the Y-electrodes 115 and the horizontal axis takes voltages applied to the X-electrodes 114. In FIG. 8, 400 indicates a state in which a voltage applied to the Wehnelt electrode 112 is applied to the XY-electrodes, and FIG. 8 shows how much voltage is increased or decreased from this state. Besides, FIG. 8 shows the size of a radiation range with respect to a specific voltage applied to the XY-electrodes in the graph (represented by a radiation range $F_{XB}$). In FIG. 8, the voltages of the X-electrodes 114 shall be increased or decreased by the same amount, and the voltages of the Y-electrodes 115 shall be increased or decreased by the same amount.

When $V_{X11}$ (kV) and $V_{Y11}$ (kV) are applied to the X-electrodes 114 and the Y-electrodes 115, respectively, the radiation range $F_{XB}$ is L11 mm square. When $V_{X12}$ (kV) and $V_{Y12}$ (kV) are applied to the X-electrodes 114 and the Y-electrodes 115, respectively, the radiation range $F_{XB}$ is L12 mm square (L12<L11), which is smaller than L11 mm square. The size of the radiation range $F_{XB}$ decreases as the voltage applied to the XY-electrodes is lowered, whereas the size of the radiation range $F_{XB}$ increases as the voltage applied to the XY-electrodes is raised.

Figure 9A:
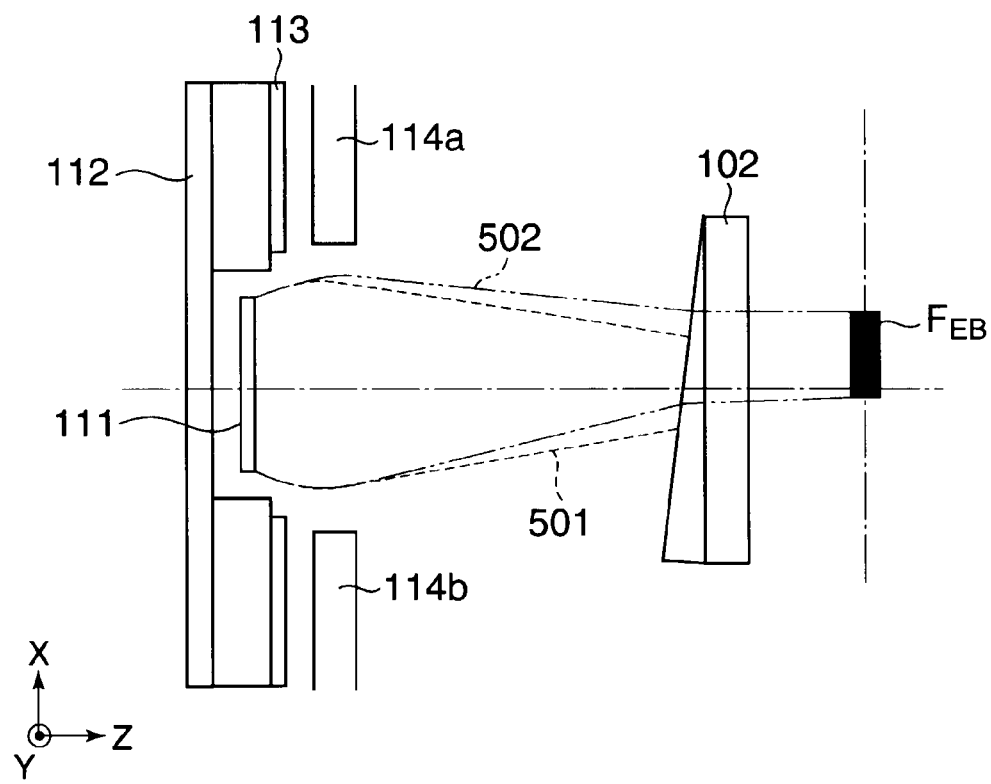
FIG. 9A is a schematic cross-sectional view on the XZ plane for describing movement in the X-axis direction of the path of an electron beam.

Next, the movement of the radiation range $F_{EB}$ will be specifically described. FIG. 9A is a schematic cross-sectional view on the XZ plane for describing the movement of the radiation range $F_{EB}$ in the X-axis direction. Moreover, FIG. 9B is a schematic cross-sectional view on the YZ plane for describing the movement of the radiation range $F_{EB}$ in the Y-axis direction.

A state in which the X-electrodes 114a and 114b have equal electric potentials shall be a reference state (a path indicated by a dotted line 501 in FIG. 9A). In this case, "equal electric potentials" may be the same electric potentials as that of the Wehnelt electrode 112, or may be electric potentials obtained by applying equal voltages to the X-electrodes 114a and 114b having the same electric potentials as the Wehnelt electrode 112. In this reference state, for example, a positive electric potential is added to the X-electrode 114a (the voltage is raised), and a negative electric potential is added to the X-electrode 114b (the voltage is lowered). Thus, as shown in FIG. 9A, it is possible to move the path of the electron beam EB in the +X-direction and move the radiation range $F_{EB}$ in the +X-direction.

On the contrary, by adding a negative electric potential to the X-electrode 114a (lowering the voltage) and adding a positive electric potential to the X-electrode 114b (raising the voltage) with respect to the reference potential, it is possible to move the path of the electron beam EB in the opposite direction to that of FIG. 9A, namely, in the −X-direction and move the radiation range $F_{EB}$ in the −X-direction.

Figure 9B:
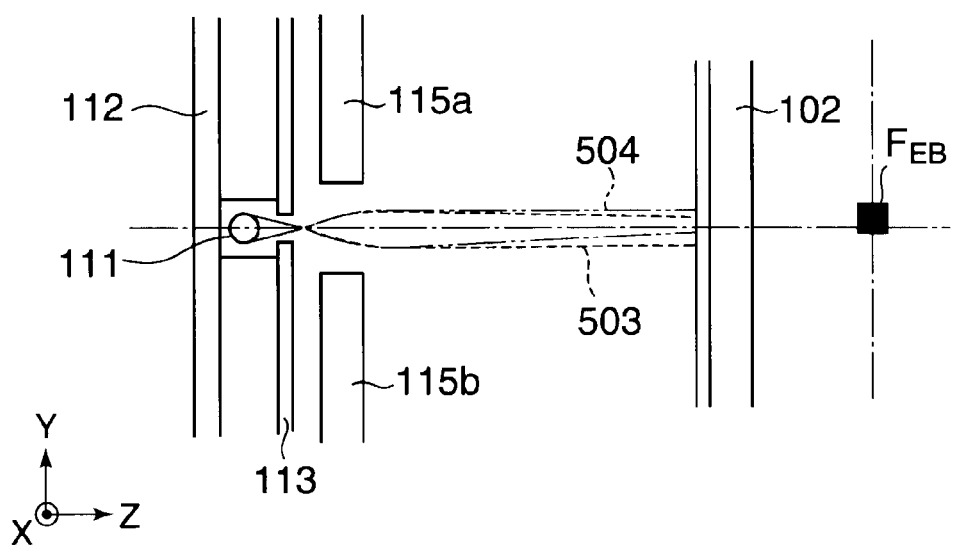
FIG. 9B is a schematic cross-sectional view on the YZ plane for describing movement in the Y-axis direction of the path of the electron beam.

Also in the Y-axis direction, a state in which the Y-electrodes 115a and 115b have equal electric potentials shall be a reference state (a path indicated by a dotted line 503 in FIG. 9B). In this case, "equal electric potentials" may be the same electric potentials as that of the Wehnelt electrode 112, or may be electric potentials obtained by applying equal voltages to the Y-electrodes 115a and 115b having the same electric potentials as the Wehnelt electrode 112. Then, in this reference state, for example, a positive electric potential is added to the Y-electrode 115a (the voltage is raised), and a negative electric potential is added to the Y-electrode 115b (the voltage is lowered). Thus, as shown in FIG. 9B, it is possible to move the path of the electron beam EB in the +Y-direction and move the radiation range $F_{EB}$ in the +Y-direction.

On the contrary, by adding a negative electric potential to the Y-electrode 115a (lowering the voltage) and adding a positive electric potential (raising the voltage) to the Y-electrode 115b with respect to the reference potential, it is possible to move the path of the electron beam EB in the opposite direction to that of FIG. 9B, namely, in the −Y-direction and move the radiation range $F_{EB}$ in the −Y-direction.

Figure 10:
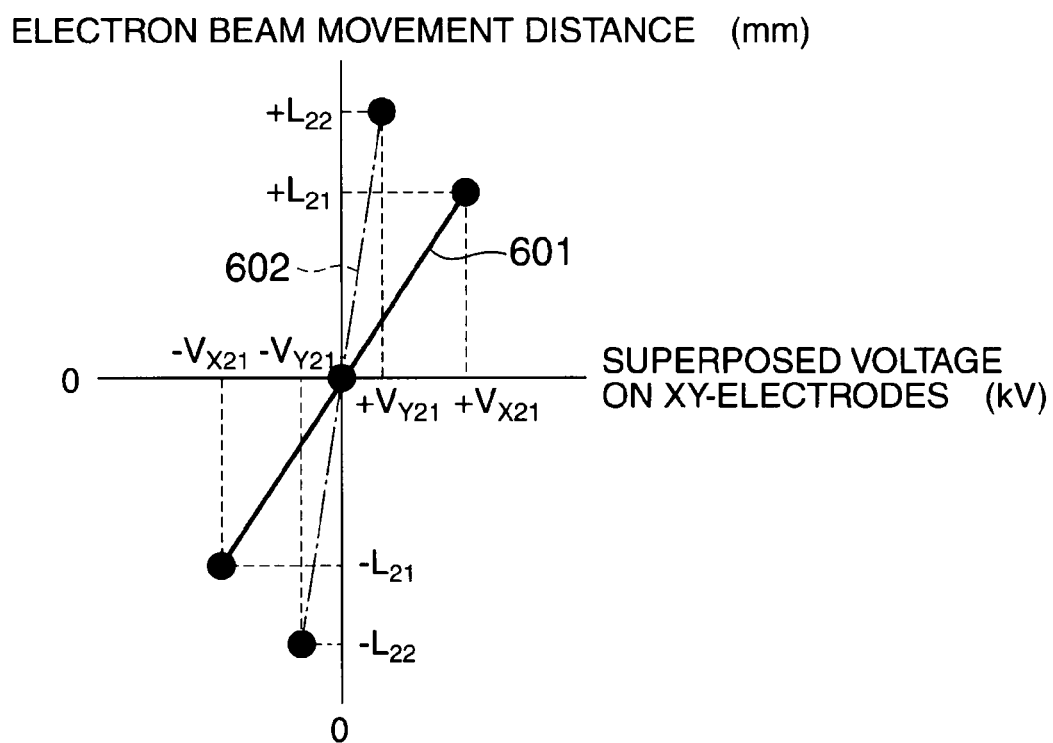
FIG. 10 is a graph showing a relation between voltages superposed on the voltages of the XY-electrodes with respect to a reference potential and a movement distance of the path of the electron beam at this moment.

Now, a relation between voltages applied to the respective XY-electrodes and a movement distance of a radiation range by movement of the path of an electron beam will be described. FIG. 10 is a graph showing a relation between voltages applied to the XY-electrodes with respect to a reference electric potential and a movement distance of the radiation range at that moment. FIG. 10 is a graph in which the horizontal axis takes voltages (kV) applied to the X-electrode 114a or the Y-electrodes 115a and the vertical axis takes a movement distance (mm) of the path of an electron beam in each of the X-axis/Y-axis directions. In FIG. 10, zero indicates a state in which voltages of the same electric potentials are applied to the XY-electrodes, and how much voltage is increased or decreased from this state is shown. FIG. 10 shows that the voltage of the X-electrode 114b is decreased when the voltage of the X-electrode 114a is increased and the voltage of the X-electrode 114b is increased when the voltage of the X-electrode 114a is decreased.

In a like manner, the voltage of the Y-electrode 115b is decreased when the voltage of the Y-electrode 115a is increased and the voltage of the Y-electrode 115b is increased when the voltage of the Y-electrode 115a is decreased. A solid line 601 represents a movement distance of the radiation range $F_{EB}$ in the X-axis direction when a voltage is superposed on that of each of the X-electrodes 114, and a dash-dot line 602 represents a movement distance of the radiation range $F_{EB}$ in the Y-axis direction when a voltage is superposed on that of each of the Y-electrodes 115.

In a state that voltages applied to the X-electrodes 114 and the Y-electrodes 115 with respect to the reference electric potential are not changed, the radiation range $F_{EB}$ does not move and therefore a movement distance is 0 (mm). When $-V_{X21}$ (kV) is applied to the X-electrode 114a and $+V_{X21}$ (kV) is applied to the X-electrode 114b, the radiation range $F_{EB}$ moves L21 (mm) in the −X-direction. When $+V_{X21}$ (kV) is applied to the X-electrode 114a and $-V_{X21}$ (kV) is applied to the X-electrode 114b, the radiation range $F_{EB}$ moves L21 (mm) in the +X-direction. When $-V_{Y21}$ (kV) is applied to the Y-electrode 115a and $+V_{Y21}$ (kV) is applied to the Y-electrode 115b, the radiation range $F_{EB}$ moves L22 (mm) in the −X-direction. When $+V_{Y21}$ (kV) is applied to the Y-electrode 115a and $-V_{Y21}$ (kV) is applied to the Y-electrode 115b, the radiation range $F_{EB}$ moves L22 (mm) in the +Y-direction.

Thus, as the voltage applied to the X-electrode 114a is increased and the voltage applied to the X-electrode 114b is decreased, the radiation range $F_{EB}$ moves in the +X-direction, whereas as the voltage applied to the X-electrode 114a is decreased and the voltage applied to the X-electrode 114b is increased, the radiation range $F_{EB}$ moves in the −X-direction. Moreover, as the voltage applied to the Y-electrode 115a is increased and the voltage applied to the Y-electrode 115b is decreased, the radiation range $F_{EB}$ moves in the +Y-direction, whereas as the voltage applied to the Y-electrode 115a is decreased and the voltage applied to the Y-electrode 115b is increased, the radiation range $F_{EB}$ moves in the −Y-direction.

As described above, by changing voltages applied to the X-electrodes 114 and the Y-electrodes 115, it is possible to change the size of the radiation range $F_{EB}$ and move the electron beam path. The electron beam emitted from the coil filament 111 may expand from the radiation center as getting farther from the coil filament 111. As a result, the electron beam path deviates more from the size of the radiation range $F_{EB}$ and position of the electron beam path for adjustment.

Therefore, at a farther place from the coil filament 111, it is more required to apply a large voltage when changing the size of the radiation range $F_{EB}$ to a desired one and moving the electron beam path.

With regard to this point, by arranging the X-electrodes 114 and the Y-electrodes 115 on the same plane, it is possible to arrange the X-electrodes 114 and the Y-electrodes 115 in proximity to the coil filament 111. Accordingly, it becomes possible to keep a voltage necessary for changing the radiation range $F_{EB}$ and moving the electron beam path both in the X-axis direction and in the Y-axis direction so as to be smaller than in the case of arranging either the X-electrodes 114 or the Y-electrodes 115 away from the coil filament 111.

Further, as described above, it is possible to regulate so as to change the size of the radiation range $F_{EB}$ to a desired size and move the electron beam path to a desired position at a low voltage. Therefore, it is possible to make a power source for supplying electricity to the respective X-electrodes 114 and Y-electrodes 115 small. Consequently, it becomes possible to decrease the size of the whole X-ray CT apparatus including the power supply.

Further, as described above, the X-electrodes 114 and the Y-electrodes 115 are arranged on the same plane near the coil filament 111 and are arranged near the coil filament 111, so that it is possible to make a distance between the coil filament 111 and the anode 102 short.

Consequently, it becomes possible to decrease the size of the whole X-ray tube 100 including the coil filament 111 and the anode 102.

Figure 11:
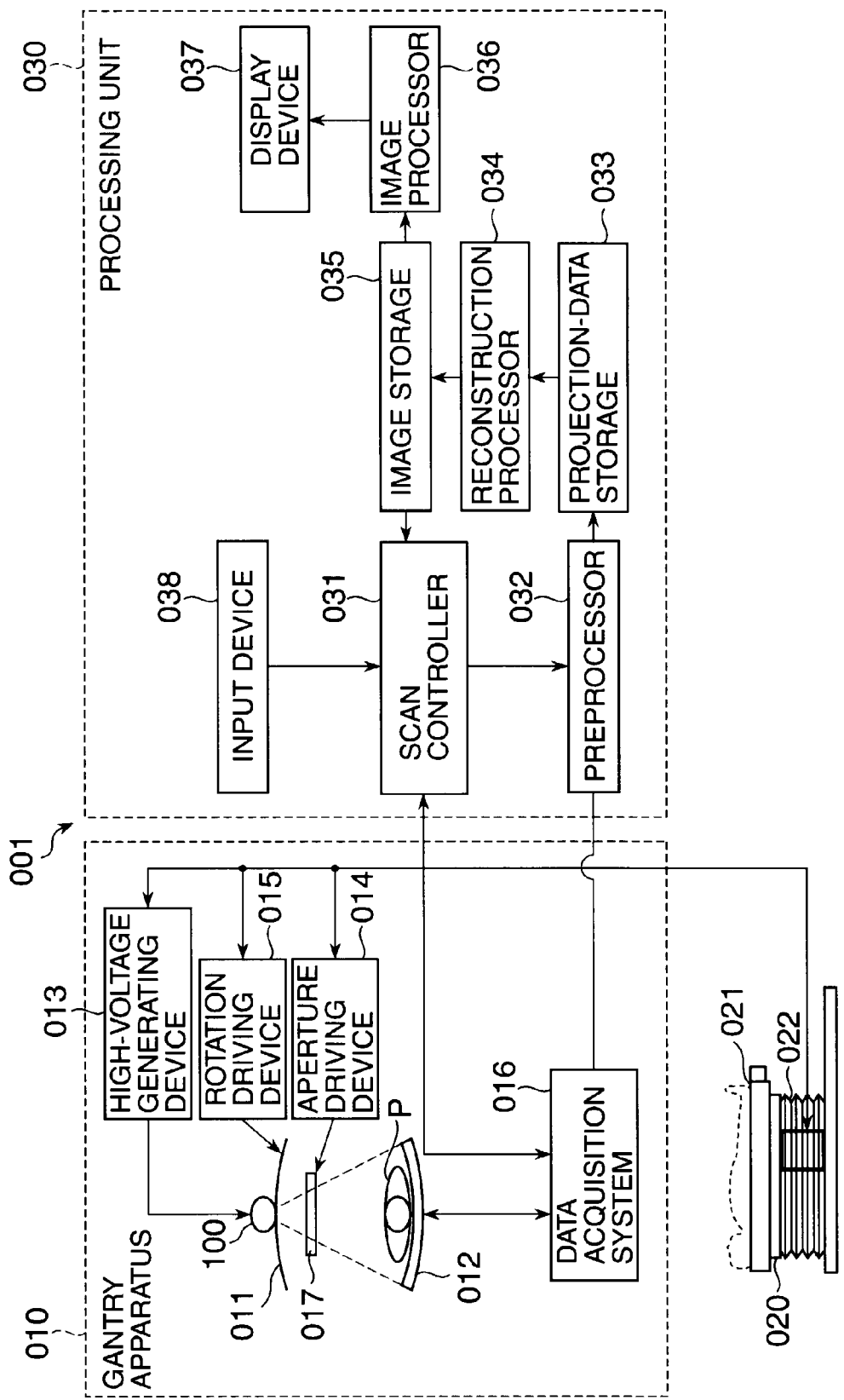
FIG. 11 is a block diagram showing a configuration of an X-ray CT apparatus equipped with the X-ray tube according to the first embodiment.

FIG. 11 is a block diagram showing a configuration of an X-ray CT apparatus equipped with the X-ray tube 100.

The X-ray CT apparatus is provided with a gantry apparatus 010, a couch apparatus 020, and a processing unit 030. The gantry apparatus 010 and the couch apparatus 020 are connected by a signal line so as to be controllable by the processing unit 030.

The gantry apparatus 010 is an apparatus configured to irradiate with majorly an X-ray and detect the radiation transmitted through a subject. This apparatus has an aperture. Within the gantry apparatus 010, a rotating gantry 011 called a gantry is housed. The X-ray tube 100 is mounted on the rotating gantry 011 so as to be paired with a detector 012. The X-ray tube 100 and the detector 012 are mounted so as to face each other across the aperture of the rotating gantry 011. Moreover, within the gantry apparatus 010, a high-voltage generating device 113 and an aperture driving device 014 are arranged in pair with the X-ray tube 100, a rotation driving device 015 is arranged in pair with the rotating gantry 011, and a data acquisition system 116 is arranged in pair with the detector 012.

The rotating gantry 011 is driven by the rotation driving device 015 to rotate about the aperture. The high-voltage generating device 013 performs supply of a heating current and application of a high voltage to the coil filament 111 of the X-ray tube 100, and application of voltages to the X-electrodes 114, the Y-electrodes 115 and the Wehnelt electrode 112, separately.

The aperture driving device 014 varies the irradiation field shape of a collimator 017 placed between the X-ray tube 100 and the detector 012, thereby narrowing down the generated radiation into a fan-beam shape or a cone-beam shape.

The detector 012 is provided with multiple rows and multiple channels of radiation detecting elements to detect radiation transmitted through a subject P and output the detected data (genuine data) as electric current signals. As the radiation detecting elements, the indirect conversion type that converts an X-ray into light with a phosphor such as a scintillator and then converts the light into electric charges with a photoelectric conversion element such as a photodiode, and the direct conversion type that utilizes photoconductive phenomenon, which is generation of electron-hole pairs by the X-ray and movement thereof to the electrode within a semiconductor, are mainly used.

The data acquisition system 016 is provided with an I-V convertor, an integrator, a preamplifier, and an A/D convertor for each of the radiation detecting elements. The data acquisition system 016 converts the electric current signals outputted from the respective radiation detecting elements into voltage signals, periodically integrates and amplifies the voltage signals in synchronization with a radiation period, and converts the signals into digital signals. The data acquisition system 016 outputs the detected data converted into the digital signals to the processing unit 030 via the signal line.

On the upper face of the base of the couch apparatus 020, a couch top 021 is mounted. On the couch top 021, the subject P is laid. The couch top 021 is configured to be driven by a couch driving device 022 to move in the aperture axis direction at a predetermined speed.

When a rotation of the rotating gantry 011 and movement of the couch top 021 are simultaneously executed, a relative movement of the X-ray tube 100 and the detector 012 to the couch top 021 forms a helical shape. Thus, a helical scan is executed. Moreover, by rotation of the rotating gantry 011 while stoppage of the couch top 021, a conventional scan or a dynamic scan is executed.

The processing unit 030 is provided with a scan controller 031, a preprocessor 032, a projection data storage 033, a reconstruction processor 034, an image storage 035, an image processor 036, a display device 037, and an input device 038.

The display device 037 is a monitor such as a CRT or a liquid crystal display, and displays a reconstructed image of the inside of the subject P. The input device 138 is an input interface such as a keyboard, a mouse and a trackball. Into the input interface, the operator performs input of imaging conditions, press of a start button placed thereon, and so on.

The scan controller 031 controls a scan in accordance with the imaging conditions inputted by using the input device 038. The imaging conditions include a whole imaging range of a subject, a range of each of sections divided in the whole imaging range, a helical pitch (HP), a rotation speed, a tube voltage (kV), a tube current (mA), the size of the radiation range $F_{EB}$, and so on.

As the scan control, various control signals are outputted at predetermined moments to the high-voltage generating device 013, the rotation driving device 015, the data acquisition system 016, the aperture driving device 014, the couch driving device 022, the preprocessor 032 and the reconstruction processor 034, whereby rotation of the rotating gantry 011, movement of the couch, the dose of the X-ray radiated by the X-ray tube 100, the size of the radiation range $F_{EB}$ emitted within the X-ray tube 100, the preprocessing of the projection data, and reconstruction of an image are controlled.

To be specific, in the control of the size of the radiation range $F_{EB}$ of electrons emitted to the anode 102 of the X-ray tube 100, the scan controller 031 controls the high-voltage generating device 013 to raise the voltages of both the X-electrodes 114$a$ and 114$b$ by the same level for making the radiation range $F_{EB}$ large-size. A like process is executed on the Y-electrodes 115.

On the other hand, for making the radiation range $F_{EB}$ small, the scan controller 031 controls the high-voltage generating device 013 to decrease the voltages of both the X-electrodes 114$a$ and 114$b$ by the same level. A like process is executed on the Y-electrodes.

Further, for moving the radiation range $F_{EB}$ in the X-axis direction, the scan controller 031 controls the high-voltage generating device 013 to apply a voltage of the same electric potential but opposite polarity to both the X-electrodes 114$a$ and 114$b$.

Further, for moving the electron beam path in the Y-axis direction, the scan controller 031 controls the high-voltage generating device 013 to apply a voltage of the same electric potential but opposite polarity to both the Y-electrodes 115$a$ and 115$b$.

In the control of the voltages on the X-electrodes and the Y-electrodes, the scan controller 031 outputs a control signal that controls an electric potential to the high-voltage generating device 013, and the high-voltage generating device 013 gives an electric potential according to the control signal.

The preprocessor 032 executes sensitivity correction for correcting the intensity of an X-ray on the genuine data, and outputs projection data PD to the projection data storage 033. Into the projection data storage 033, projection data outputted from the preprocessor 032 is stored. Each projection data is provided with a view number. The view number indicates an angle at which an X-ray is radiated. For example, in the X-ray CT apparatus, when the X-ray tube 100 radiates an X-ray n number of times while the rotating gantry 011 rotates once, the X-ray radiation angle is divided into 360/n, and a view number is given in accordance with the division.

The reconstruction processor 134 reconstructs an image within the subject P by back projection of the projection data. By a reconstruction process by image reconstruction algorithm typified by the Feldkamp method, this reconstruction processor 134 executes back projection of the projection data read out from the projection data storage 133, and reconstructs the inside of the subject P as image data.

The reconstructed image data is inputted and stored into the image storage 035.

The image processor 036 executes various kinds of image processing such a scan conversion process of converting the image data stored in the image storage 035 into a video format of orthogonal coordinate system, and generates a display image. The display device 037 displays the display image generated by the image processor 136.

As described above, the X-ray tube according to this embodiment has such a configuration that a blocking member that blocks an extra electron beam is arranged near the electron beam outlet of the Wehnelt electrode and the XY-electrodes are arranged on the same plane near the filament that emits an electron beam.

With the configuration including the aperture, it is possible to block the outer part of the emitted electron beam. Consequently, it is possible to reduce an electron beam that causes a blur of a focal point, and it is possible to form a more accurate focal point with less blur.

That is to say, electrons emitted from the periphery of the cross section of the filament can be blocked by the projecting part, and occurrence of a blur in the electron beam radiated to the anode is restricted. Moreover, it is possible to make the X-ray tube smaller in size than in the case of arranging the first electrode member and the second electrode member in different positions on the electron beam path. Moreover, the arrangement of the electrodes near the filament can reduce a voltage applied to the electrodes for changing the size of the radiation range of the electron beam and moving the electron beam path.

Besides, since the reduction of the voltage applied to the electrodes can make a power source for supplying electricity to the electrodes small in size, it is possible to make the X-ray tube smaller in size.

Further, a distance between the filament and the anode that is necessary for arrangement of the XY-electrodes can be shorter, and the X-ray tube can be smaller in size.

Furthermore, since both the XY-electrodes are arranged near the filament, the voltages applied to the XY-electrodes for changing the size of the radiation range and moving the electron beam path with respect to the electron beam emitted from the filament can be kept small. Besides, it is consequently possible to make a power supply for supplying electricity to the XY-electrodes small in size and make the whole X-ray CT apparatus small in size.

Second Embodiment

Below, an X-ray tube according to a second embodiment of the present invention will be described. The X-ray tube according to this embodiment is different from that of the first embodiment in configuration of being capable of applying voltages higher than a voltage of the coil filament to the Wehnelt electrode and the aperture.

Thus, hereinafter, application of high voltages to the Wehnelt electrode and the aperture and an effect of the application will be mainly described. In the following description, function parts denoted by the same reference numerals as in the first embodiment shall have the same functions unless otherwise described.

The aperture 113 and the Wehnelt electrode 112 in this embodiment are configured to be capable of receiving voltages from the high-voltage generating device 013 serving as a voltage supply source.

In this case, the aperture 113 and the Wehnelt electrode 112 are configured to be capable of receiving voltages separately from the coil filament 111 and the XY-electrodes. The aperture 113 and the Wehnelt electrode 112 are capable of receiving supply of considerably larger voltages than the coil filament 111. In this embodiment, the Wehnelt electrode 112 and the aperture 113 are configured to receive the same voltages but can also be configured to receive different voltages separately.

In execution of control of an electron beam such as movement of the path of the electron beam, in a case that the electron beam emitted from the coil filament 111 is radiated to the anode 102 at all times, the electron beam will continuously move with respect to a subject. If the electron beam continuously moves in this manner, so-called tailing occurs, which is a phenomenon that a white line appears in an image.

The occurrence of tailing in an image makes accurate diagnosis difficult. Thus, it is desirable that the electron beam is radiated onto the anode 102 at a time point that movement of the path of the electron beam is completed in the X-ray CT apparatus.

Also in this embodiment, in a normal electron beam emission state, the scan controller 031 controls the high-voltage generating device 013 to apply a voltage of about −tens of kilovolts to the coil filament 111 and apply voltages of a few kilovolts negatively higher than that of the coil filament 111 to the Wehnelt electrode 112 and the aperture 113.

Then, at a time to transmit, to the high-voltage generating device 013, a control signal for moving the path of the electron beam, namely, a control signal applied to the XY-electrodes for changing the voltages for moving the path of the electron beam (a time to start movement of the electron beam), the scan controller 031 transmits a control signal for applying the voltages to the Wehnelt electrode 112 and the aperture 113, to the high-voltage generating device 013. The scan controller 031 may be configured to transmit the signal for controlling the Wehnelt electrode 112 and the aperture 113 earlier than the signal for controlling the XY-electrodes.

Then, at a time that the movement of the path of the electron beam is completed, the scan controller 031 transmits a control signal for applying the voltages to the Wehnelt electrode 112 and the aperture 113 to the high-voltage generating device 013. As the time that the movement of the path of the electron beam is completed, the scan controller 031 may previously store a statistically calculated time, or the scan controller 031 may determine that the movement of the path of the electron beam is completed upon reception of information that the movement of the position of the radiation range $F_{EB}$ stops after measurement of the position of the radiation range $F_{EB}$.

In the normal electron beam emission state, to the Wehnelt electrode 112 and the aperture 113, voltages of about −tens of kilovolts are applied.

Upon control by the scan controller 031 for starting the movement of the path of the electron beam, voltages are applied to the Wehnelt electrode 112 and the aperture 113 at a time that the movement of the electron beam path is started. In the X-ray tube 100 according to this embodiment, the aperture 113 projects enough to block the outer part of the emitted electron beam, and consequently, a high voltage is applied to between the Wehnelt electrode 112 and the aperture 113 with little gap. By the voltages applied to the Wehnelt electrode 112 and the aperture 113, the electrons of −tens of kilovolts emitted from the coil filament 111 are repelled toward the coil filament 111, and the electrons radiated from the coil filament 111 are suppressed not to be radiated outside from the inside covered by the Wehnelt electrode 112 and the aperture 113. Consequently, the X-ray tube 100 can cut off the electron beam radiated from the coil filament 111 toward the anode 102.

Then, upon control by the scan controller 031 after the movement of the path of the electron beam ends, voltages of −tens of kilovolts are applied to the Wehnelt electrode 112 and the aperture 113. Consequently, cut-off of the electrons emitted from the coil filament 111 by the high voltages is released, and the electron beam is radiated to the anode 102.

Figure 12:
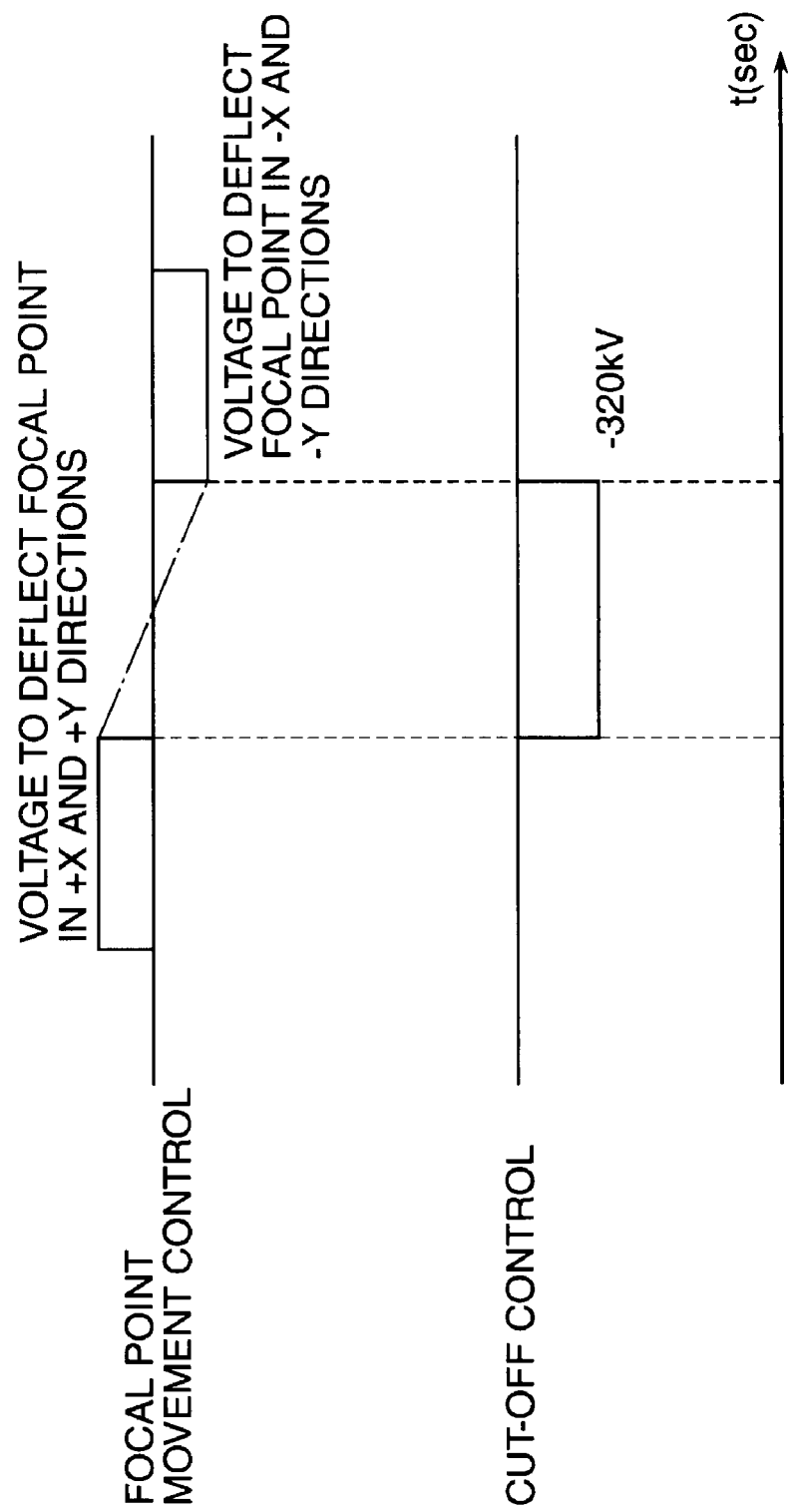
FIG. 12 is a view for describing a time to apply a high voltage to the Wehnelt electrode and the aperture for current cut-off.

FIG. 12 is a view for describing a time to apply high voltages to the Wehnelt electrode 112 and the aperture 113 for cut-off of an electric current. FIG. 12 shows a change from a state in which voltages for deflecting the electron beam in the +XY-directions are applied to the XY-electrodes to a state in which voltages for deflecting the electron beam in the −XY-directions are applied to the XY-electrodes. In FIG. 12, the top line shows a state of a voltage applied to the XY-electrodes before and after the movement of the path of the electron beam, the middle line shows a state in which a cut-off voltage is applied to the Wehnelt electrode 112 and the aperture 113, and the bottom line shows the passage of time. As shown in FIG. 12, the cut-off voltage is applied to the Wehnelt electrode 112 and the aperture 113 at a time that voltage change on the XY-electrodes of a specific state for moving the path of the electron beam is started, and the application of the cut-off voltage to the Wehnelt electrode 112 and the aperture 113 ends at a time that the movement of the path of the electron beam ends and the voltage change on the XY-electrodes for moving the path of the electron beam ends.

Figure 13:
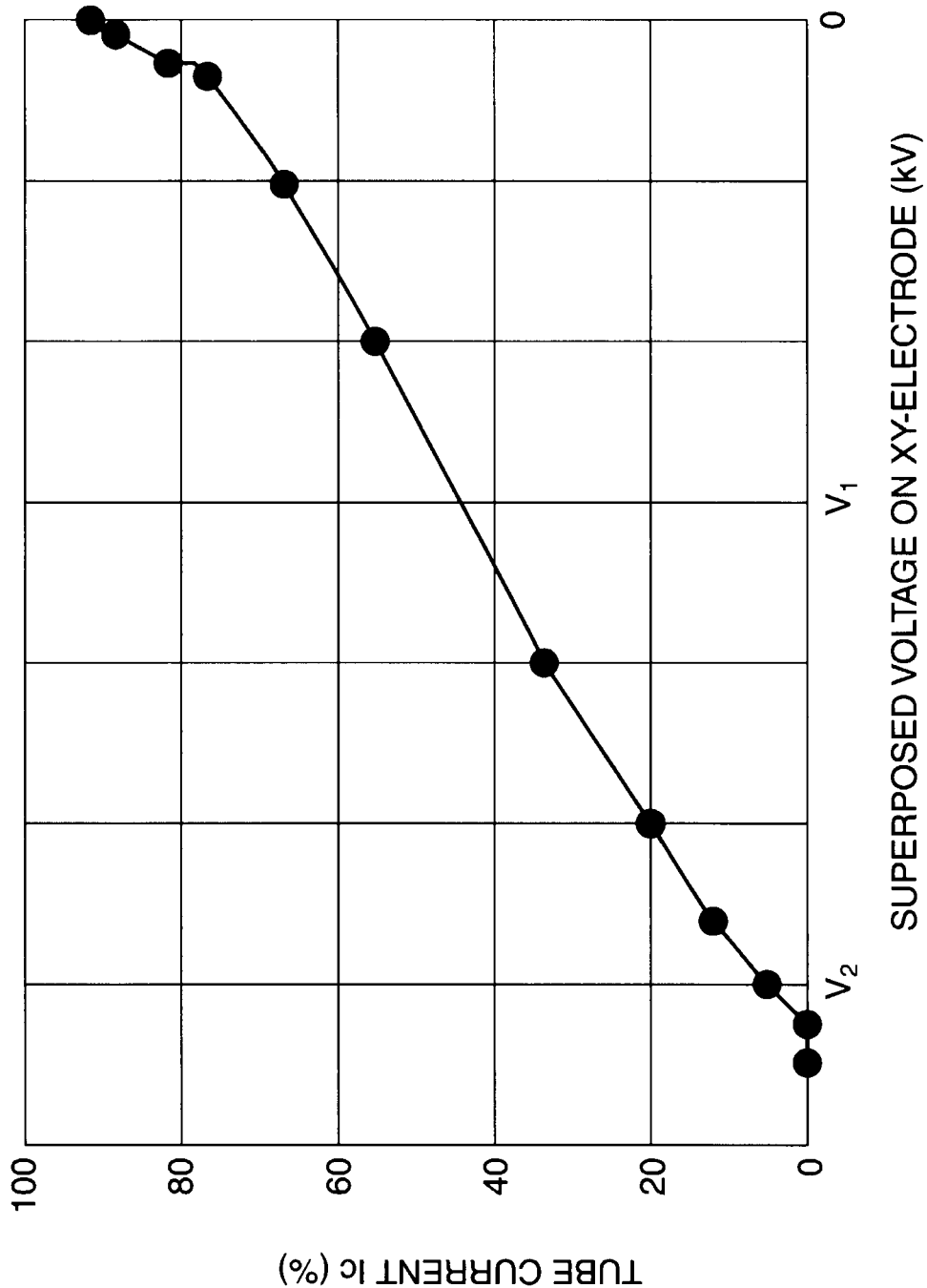
FIG. 13 is a graph showing a relation between a voltage applied to the Wehnelt electrode and aperture and the percentage of a tube current reaching the aperture.

With reference to FIG. 13, a relation between application of voltages to the Wehnelt electrode 112 and the aperture 113 and a tube current will be described. FIG. 13 is a graph showing a relation between voltages applied to the Wehnelt electrode 112 and the aperture 113 and the percentage of the tube current reaching the anode 102. In the graph of FIG. 13, the vertical axis takes the percentage (%) of the tube current reaching the anode 102 with respect to the tube current radiated from the coil filament 111, and the horizontal axis takes a voltage (kV) applied to the Wehnelt electrode 112 and the aperture 113.

As shown in FIG. 13, when a voltage applied to the Wehnelt electrode 112 and the aperture 113 is −V1 kV, approximately 45% of the tube current reaches the anode 102. When a voltage applied to the Wehnelt electrode 112 and the aperture 113 is −V2 kV or less, which is lower voltage than V1 kV, the tube current reaching the anode 102 is almost zero. Thus, in this embodiment, when a voltage of −V2 kV is applied to the Wehnelt electrode 112 and the aperture 113, an electron beam can be mostly cut off. In this embodiment, since the tube current is almost zero at −V2 kV as shown in FIG. 13, a voltage applied to the Wehnelt electrode 112 and the aperture 113 during movement of an electronic beam path shall be −V2 kV. As far as the tube current can be almost zero, the voltage may be another voltage. For example, it is possible to use a lower voltage when the voltage of the coil filament is low.

Then, in an X-ray CT apparatus using the X-ray tube 100 described above, in a like manner as in the first embodiment, an X-ray CT image can be generated by the gantry apparatus 010, the couch apparatus 020, and the processing unit 030.

As described above, the X-ray tube according to this embodiment is configured to be capable of applying a higher voltage than electrons emitted from the coil filament to the Wehnelt electrode and the aperture at a time to move the path of the electronic beam. Consequently, the electrons emitted from the coil filament are suppressed, the electron beam is not radiated to the anode during movement of the electron beam path, and the X-ray is not radiated to the outside of the X-ray tube, with the result that it is possible to reduce an influence on image formation by the electrons emitted during movement of the electron beam path, and it is possible to restrict tailing to generate a favorable image.

Third Embodiment

Figure 14:
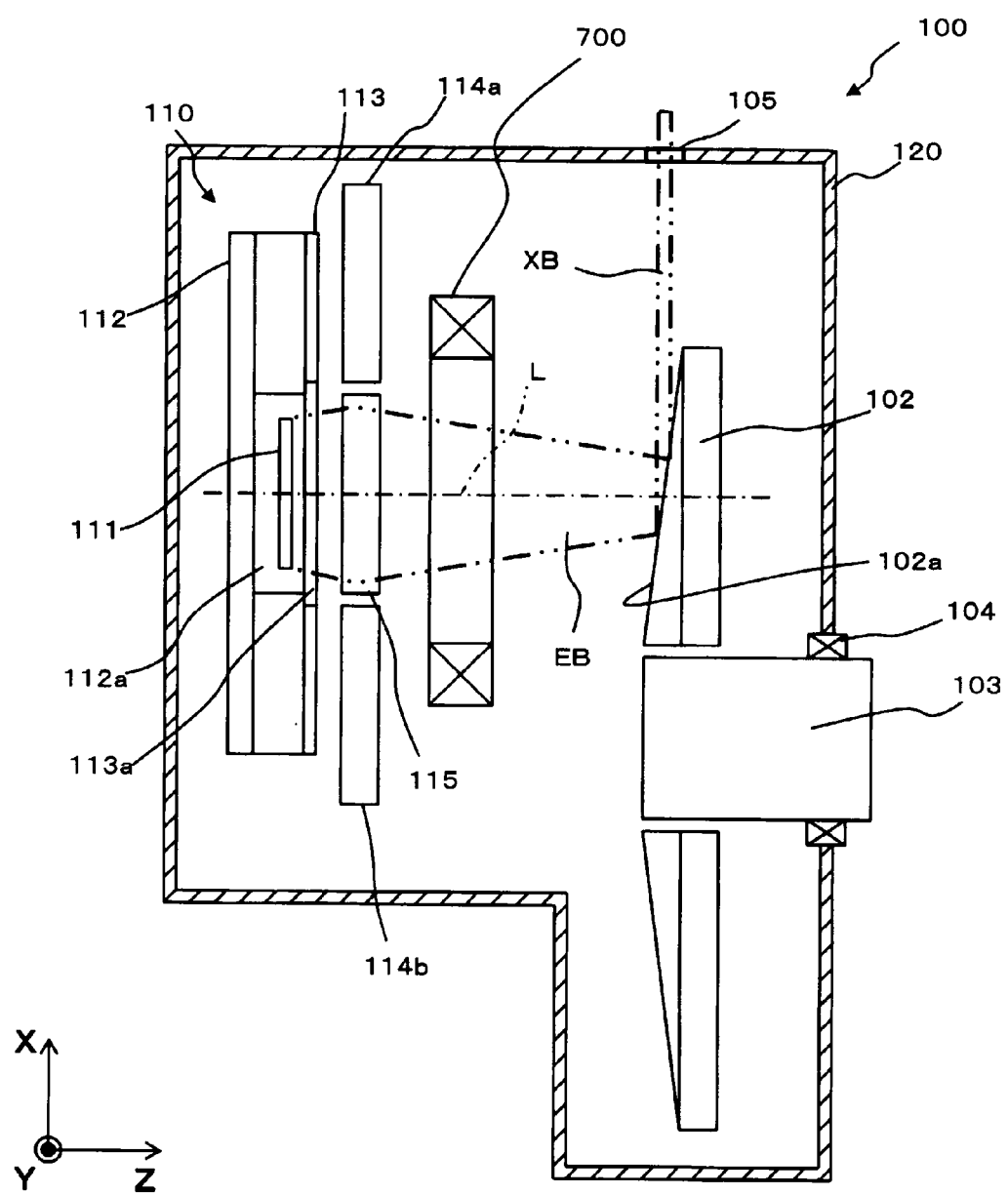
FIG. 14 is a cross-sectional view on the XZ plane of an X-ray tube in the state of radiating an X-ray according to a second embodiment.

Hereinafter, an X-ray tube according to a third embodiment of the present invention will be described. The X-ray tube according to this embodiment is different from that of the first embodiment in configuration including an electromagnetic deflector for moving an electron beam path. Below, the configuration and action of the electromagnetic deflector for moving the electron beam path will be mainly described. FIG. 14 is a cross-sectional view on the XZ plane of a state of the X-ray tube radiating an X-ray according to this embodiment.

Figure 15:
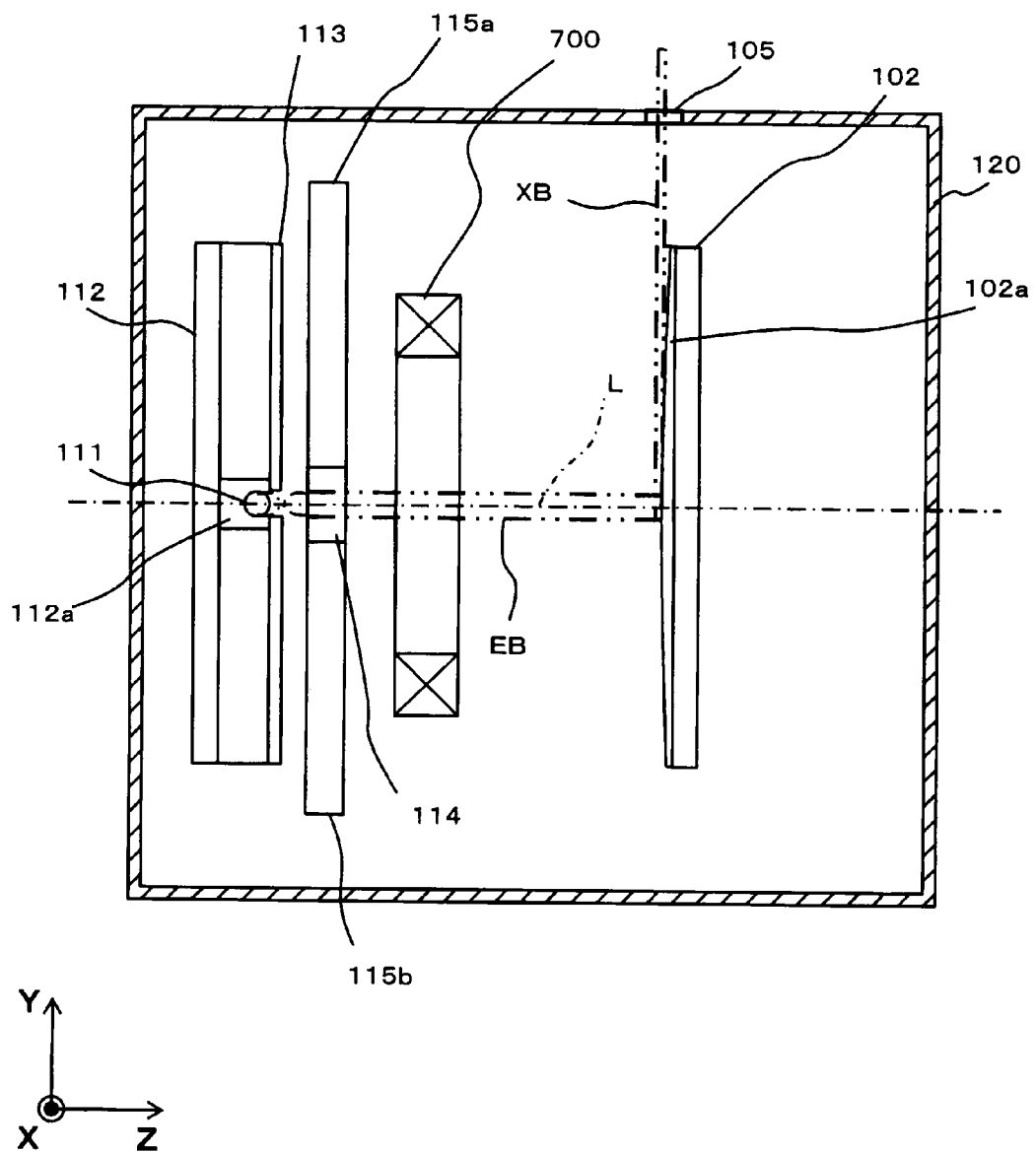
FIG. 15 is a cross-sectional view on the YZ plane of the X-ray tube in the state of radiating an X-ray according to the second embodiment.

FIG. 15 is a cross-sectional view on the YZ plane of a state of the X-ray tube radiating an X-ray according to this embodiment. In the following description, function parts denoted by the same reference numerals as in the first embodiment shall have the same function unless otherwise described.

Figure 16:
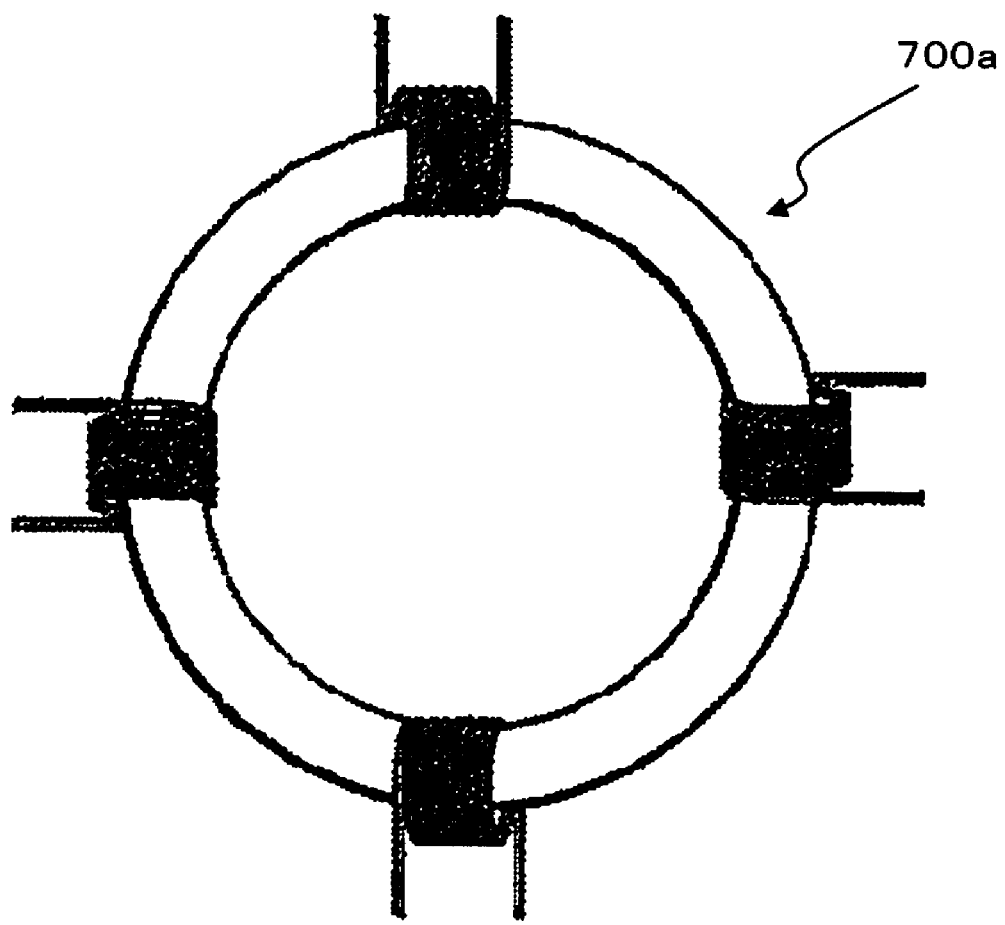
FIG. 16 is a schematic view of a toroidal coil as an example of an electromagnetic deflector.

The X-ray tube 100 according to this embodiment has the X-electrodes 114 and the Y-electrodes 115 on the same plane near the coil filament 111 between the coil filament 111 and the anode 102 as in the first embodiment. Besides, in the X-ray tube 100 according to this embodiment, an electromagnetic deflector 700 is arranged between the XY-electrodes and the anode 102. Although a toroidal coil 700a shown in FIG. 16 is used as the electromagnetic deflector 700 in this embodiment, an electromagnetic deflector having another structure, for example, an electromagnetic deflector having a saddle coil structure may be used. FIG. 16 is a schematic view of the toroidal coil 700a as an example of the electromagnetic deflector 700.

In this embodiment, the size of a radiation range is changed by the XY-electrodes, and the electron beam path is moved by the electromagnetic deflector 700. That is to say, voltages applied to the XY-electrodes for changing the size of the radiation range are changed, a voltage to move the electron beam path thereafter is not changed, and a voltage is applied to the electron beam deflector 700, whereby movement of the electron beam path is executed. Below the operation of the electromagnetic deflector 700 and the XY-electrodes will be specifically described.

The electromagnetic deflector 700 has the toroidal coil 700a disposed so as to surround the path L so that the central axis thereof coincides with the path L. The electromagnetic deflector 700 generates a large electromagnetic field by reception of voltage from an external electric power supply. Then, the electromagnetic deflector 700 moves the path of the electron beam EB via a magnetic field by the generated electromagnetic field. The movement of the path of the electron beam EB is deflection of the electron beam.

Further, the X-electrodes 114 and the Y-electrodes 115 in this embodiment are used only for changing the size of the radiation range $F_{EB}$. The scan controller 031 controls the X-electrodes 114 and the Y-electrodes 115 to change voltages only at the time of size change, and does not change the voltages of the X-electrodes 114 and the Y-electrodes 115 in control for moving the electron beam. That is to say, considering a voltage applied to the Wehnelt electrode 112 as a reference voltage, only change of a voltage for changing the size of the radiation range $F_{EB}$ is executed with respect to the reference voltage.

Then, in an X-ray CT apparatus using the X-ray tube 100 described above, an X-ray CT image is generated by the gantry apparatus 010, the couch apparatus 020, and the processing unit 030, in a like manner as in the first embodiment.

As described above, the X-ray tube according to this embodiment is configured to regulate the size of the radiation range by the XY-electrodes and move the path of the electron beam by the electromagnetic deflector. Because using the electromagnetic deflector, this X-ray tube has a larger structure than that of the first embodiment, but does not need to execute a voltage change control for deflecting the electron beam on the XY-electrodes. Consequently, it is possible to limit variation of a voltage applied to the coil filament, and an electric current generated from the coil filament is stabilized. That is to say, control of the electron beam is facilitated, and stable movement of the electron beam is enabled.

Electrons emitted from the periphery of the cross section of the filament can be blocked by the projecting part, and occurrence of blur of an electron beam radiated to the anode is suppressed. Also, control becomes easier than in the case of moving an electron beam path by the first electrode member and the second electrode member, and it is possible to move an electron beam path with stability.

Although this embodiment has been described based on the first embodiment above, this embodiment is operable when the function thereof is added to the second embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray tube, comprising:
   a Wehnelt electrode having a dent inside;
   a filament arranged in the dent of the Wehnelt electrode and configured to emit an electron beam when electricity is passed therethrough;
   an anode configured to emit an X-ray in response to the incident electron beam;
   an electrode part configured by at least one pair of electrode members, the electrode members facing each other across a path of the electron beam, a voltage being applied to each of the electrode members;
   a voltage controller configured to control the voltage applied to the electrode part; and
   a shield member arranged in contact with the Wehnelt electrode and configured to cover part of the dent by a projecting part.

2. The X-ray tube according to claim 1, wherein:
   the dent is a groove formed on the Wehnelt electrode, and the filament is arranged along the groove;
   the electrode part has a pair of first electrode members and a pair of second electrode members;
   the first electrode members are arranged facing each other, the second electrode members are arranged facing each other, a direction along which the first electrode members face is orthogonal to a direction along which the second electrode members face, and voltages are applied to the respective electrode members; and
   the voltage controller is configured to:
   by controlling the voltages applied to the first electrode members, control change of a size in a first direction of a radiation range of the electron beam on the anode and movement of the electron beam in the first direction; and
   by controlling the voltages applied to the second electrode members, control change of a size in a second direction orthogonal to the first direction of the radiation range of the electron beam on the anode and movement of the electron beam in the second direction.

3. The X-ray tube according to claim 2, wherein both the first electrode members and the second electrode members are arranged on a same plane perpendicular to a radiation direction of the electron beam.

4. The X-ray tube according to claim 2, wherein the filament is a coil filament, the filament is arranged so that a plane including a diameter direction of a coil includes the second direction, and a length of the first direction of the coil is longer than the diameter of the coil.

5. The X-ray tube according to claim 3, wherein the voltage controller is configured to, in a state of already applying voltages to the first electrode members and the second electrode members:
   by changing a voltage applied in a same electric potential state to each of the first electrode members, change the size of the radiation range of the electron beam on the anode in the first direction; and
   by changing a voltage applied in a same electric potential state to each of the second electrode members, change the size of the radiation range of the electron beam on the anode in the second direction.

6. The X-ray tube according to claim 3, wherein the voltage controller is configured to, in a state of already applying voltages to the first electrode members and the second electrode members:
   by raising a voltage applied to one of the first electrode members from a voltage applied thereto at present and lowering a voltage applied to the other from a voltage applied thereto at present, move the electron beam toward one or the other of the first electrode members; and
   by raising a voltage applied to one of the second electrode members from a voltage applied thereto at present and lowering a voltage applied to the other from a voltage applied thereto at present, move a focal point of the electron beam toward one or the other of the second electrode members.

7. The X-ray tube according to claim 1, wherein:
   the Wehnelt electrode and the shield member are configured so that voltages can be applied thereto; and
   the voltage controller is configured to apply a lower voltage than a voltage applied to the filament to the Wehnelt electrode and the shield member to thereby cut off entrance of the electron beam emitted from the filament to the anode.

8. The X-ray tube according to claim 1, further comprising, between the electrode part and the anode on the path of the electron beam, an electromagnetic deflector configured to deflect the path of the electron beam arranged so as to surround the path of the electrode beam.

9. An X-ray CT apparatus, comprising an X-ray tube configured to radiate an X-ray, a detector configured to detect the X-ray radiated from the X-ray tube, a reconstruction part configured to reconstruct an image from projection data based on detection by the detector, and a controller configured to control a scan by detection of the X-ray including control of the X-ray tube, wherein the X-ray tube includes:
- a Wehnelt electrode having a dent inside;
- a filament arranged in the dent of the Wehnelt electrode and configured to emit an electron beam when electricity is passed therethrough;
- an anode configured to emit an X-ray in response to the incident electron beam;
- an electrode part configured by at least one pair of electrode members, the electrode members facing each other across a path of the electron beam, a voltage being applied to each of the electrode members;
- a voltage controller configured to control the voltage applied to the electrode part; and
- a shield member arranged in contact with the Wehnelt electrode and configured to cover part of the dent by a projecting part.

* * * * *